US006925394B2

(12) United States Patent
Ramakrishnan et al.

(10) Patent No.: US 6,925,394 B2
(45) Date of Patent: Aug. 2, 2005

(54) CRYSTAL STRUCTURE OF THE 30S RIBOSOME

(75) Inventors: Venkatraman Ramakrishnan, Cambridge (GB); Ditlev Egeskov Brodersen, Cambridge (GB); Andrew Philip Carter, Cambridge (GB); Brian Thomas Wimberly, Kalamazoo, MI (US); William Melvon Clemons, Jr., Boston, MA (US)

(73) Assignees: University of Utah Research Foundation, Salt Lake City, UT (US); Medical Research Council, London (GB)

( * ) Notice: Subject to any disclaimer, the term of this patent is extended or adjusted under 35 U.S.C. 154(b) by 100 days.

(21) Appl. No.: 09/904,779

(22) Filed: Jul. 13, 2001

(65) Prior Publication Data

US 2002/0106660 A1 Aug. 8, 2002

(30) Foreign Application Priority Data

Jul. 14, 2000 (GB) .............................................. 0017376
Sep. 19, 2000 (GB) .............................................. 0022943

(51) Int. Cl.$^7$ ......................... G06F 19/00; G01N 33/48; C07K 14/00
(52) U.S. Cl. ........................... 702/27; 702/19; 702/530; 702/350
(58) Field of Search .................... 702/19, 27; 530/350; 436/4

(56) References Cited

PUBLICATIONS

Jan Drenth, Principles of Protein X–ray Crystallography, 1995, Springer–Verlag, p. 16.*
News Focus, Science, Nov. 1, 2002, vol. 298, pp. 948–950.*
Bhuyan, B. K, et al. (1961). "Pactamycin, A New Antitumor Antibiotic: Discovery and Biological Properties," *Antimicrob Agents Chemother* 184–190.

Böck, A. et al. (1979). "Ribosomal Ambiguity (Ram) Mutations Facilitate Dihydrostreptomycin Binding to Ribosomes," *FEBS Letters* 104(2):317–321.

Brink, M. F. et al. (1994). "Spectinomycin Interacts Specifically with the Residues G1064 and C1192 in 16S rRNA, Thereby Poteentially Freeaing This Molecule Into an Inactive Conformation," *Nucleic Acids Res* 22(3):325–331.

Brodersen et al. "the Structural Basis for th e Action of the Antibiotics Tetracycline, Pactamycin and Hygromycin B on the 30S Ribosomal Subunit," *Cell* 103:1143–1154 (2000).

Brown, C. M. et al. (1993). "Two Regions of the Escherichia Coli 16S Ribosomal RNA Are Inportant for Decoding Stop Signals in Polypeptide Chain Termination," *Nucleic Acids Res* 21(9):2109–2115.

Cabanas, M. J. et al. (1978). "Inhibition of Ribosomal Translocation by Aminoglycoside Antibiotics," *Biochem Biophys Res Commun* 83(3):991–997.

Carter et al. (2000). "Functional Insights from the Structure of the 30S Ribosomal Subunit and its Interactions with Antibiotics," *Nature* 407:340–348.

(Continued)

*Primary Examiner*—Ardin H. Marschel
*Assistant Examiner*—Cheyne D Ly
(74) *Attorney, Agent, or Firm*—Kathleen M. Williams; Palmer & Dodge LLP

(57) ABSTRACT

The invention provides an X-ray crystal structure of the 30S ribosome, obtained from *Thermus thermophilus* 30S subunit, having a tetragonal space group P4$_1$2$_1$2 with unit cell dimensions of a=401.4±4.0 Å, b=401.4±4.0 Å, c=175.9±5.0 Å. An advantageous feature of the structure is that it diffracts beyond 3 Å resolution. The invention also provides a crystal of 30S having the three dimensional atomic coordinates of the 30S ribosome, the coordinates being provided in Tables 1A and 1B. The data may be used for the rational design and modelling of inhibitors for the 30S ribosome, which have potential use as antibiotics.

3 Claims, 1 Drawing Sheet

OTHER PUBLICATIONS

Chopra, I. et al. (1992). "Tetracyclines, Molecular and Clinical Aspects," *J. Antimicrob Chemother* 29:245–277.

Clemons, Jr., W. et al. (1999). "Structure of a Bacterial 30S Ribosomal Subunit at 5.5 Å Resolution," *Nature* 400:833–840.

Clemons, Jr., W. et al. (2001). "Crystal Structure of the 30S Ribosomal Subunit from Thermus Thermophilus: Purification, Crystallization and Structure Determination," *J. Mol. Biol.* 310:827–843.

Cohen, L. B. et al. (1969). "Inhibition by Pactamycin of the Initiation of Protein Synthesis. Effect on the 30S Ribosomal Subunit," *Biochemistry* 8(4):1327–1335.

De la Fortelle, E. and Bricogne, G. (1997). "Maximum–Likelihood Heavy–Atom Parameter Refinement for Multiple Isomorphous Replacement and Multiwavelength Anamalous Diffraction Mehods," In *Methods in Enzymology*, eds. Carter, C. W., Jr. Sweet, R. M, Academic Press, New York, 1997, pp. 472–493.

Donner, D. and Kurland, C. G. (1972). "Changes in the Primary Structure of a Mutationally Altered Ribosomal Protein S4 of *Escherichia coli,*" *Mol Gen Genet* 115:49–53.

Egebjerg, J. and Garrett, R. A. (1991). "Binding Sites of the Antibiotics Pactamycin and Celesticetin on Ribosomal RNAs," *Biochimie* 73:1145–1149.

Eustice, D. C and Wilhelm, J. M. (1984). "Mechanisms of Action of Aminoglycoside Antibiotics in Eucaryotic Protein Synthesis," *Antimicrob Agents Chemother* 26(1):53–60.

Eustice, D. C. and Wilhelm, J. M. (1984). "Fidelity of the Eukaryotic Codon–Anticodon Interaction: Interference by Aminoglycoside Antibiotics," *Biochemistry* 23:1462–1467.

Fourmy, D. et al. (1996). "Structure of the A Site of *Escherichia coli* 16S Ribosomal RNA Complexed with an Aminoglycoside Antibiotic," *Science* 274:1367–1371.

Funatsu, G. and Wittmann, H. G. (1972). "Location of Amino–Acid Replacements in Protein S12 Isolated from *Escherichia coli* Mutants Resistant to Streptomycin," *J. Mol Biol* 68:547–550.

Funatsu, G. et al. (1972). "Ribosomal Proteins. XXXI. Comparative Studies on Altered Proteins S4 of Sic *Escherichia coli* Revertants from Streptomycin Dependence," *Mol Gen Genet* 115:131–149.

Geigenmüller, U. and Nierhaus, K. H. (1986). "Tetracycline Can Inhibit tRNA Binding to the Ribosomal P Site as Well as to the A Site," *Eur. J. Biochem* 161:723–726.

Gonzales, A. et al. (1978). "Studies on The Mode of Action of Hygromycin B, An Inhibitor of Translocation in Eukaryotes," *Biochim Biophys Acta* 521:459–469.

Gravel, M. et al. (1987). "Cross–Linking of Streptomychin to the 16S Ribosomal RNA of *Escherichia coli,*" *Biochemistry* 26:6227–6232.

Hope, H. et al. (1989). "Cyrocrystallography of Ribosomal Particles," *Acta Cryst.* B45:190–199.

Ito, T. and Wittmann, H. G. (1973). "Amino Acid Replacements in Proteins S5 and S12 of Two *Escherichia coli* Revertants from Streptomycin Dependence to Independence," *Mol. Gen. Genet,* 127:19–32.

Kolesnikov, I. V. et al. (1996). "Tetracyclines Induce Changes in Accessibility of Ribosomal Proteins to Proteases," *Biochimie* 78:868–873.

Harland, C. G. et al. (1996). "Limitations of Translational Accuracy" Chapter 65 In *Escherichia Coli andSalmonella, Cellular and Molecular Biology*, Second Edition, vol. 2, Neidhart,F. C. et al., eds. American Society for Microbiology Press, Washington D.C., pp. 979–1004. Includes Table of Contents.

Leclerc, D. et al. (1991). "Mutations in the 915 Region of *Escherichia coli* 16S Ribosomal RNA Reduce the Binding of Streptomycin to the Ribosome," *Nucleic Acids Res.* 19(14):3973–3977.

Manavathu, E. K. et al. (1990). "Molecular Studies on the Mechanism of Tetracycline Resistance Mediated by Tet(O)," *Antimicrob Agents Chemother* 34(1):71–77.

Mann, R. L. and Bromer, W. W. (1958). "Isolation of a Second Antibiotic from Streptomyces Hygroscopicus," *J. Am. Chem. Soc.* 80:2714–2716.

Melancon, P. et al. (1984). "Cross–Lining of Streptomycin to the 30S Subunit of *Escherichia coli* with Phenyldiglyoxal," *Biochemistry* 23:6697–6703.

Melancon, P. et al. (1988). "A Mutation in the 530 Loop of *Escherichia coli* 16S Ribosomal RNA Causes Resistance to Streptomycin," *Nucleic Acids Res* 16(2):9631–9339.

Moazed, D. and Noller, H. F. (1987). "Interaction of Antibiotics with Functional Sites in 16S Ribosomal RNA," *Nature* 337:389–394.

Montadon, P. E. et al. (1985). "Streptomycin–Resistance of Euglena Gracilis Chloroplasts: Identification of a Point Mutation in the 16S rRNA Gene in an Invariant Position," *Nucleic Acids Res.* 13(12):4299–4310.

Montandon, P. E. et al. (1986). "*E. coli* Ribosomes with a C912 to U Base Change in the 16s rRNA are Streptomycin Resistant," *EMBO J.* 5(3):3705–3708.

Mueller, F. and Brimacombe, R. (1997). "A New Model for the Three–Dimensional Folding of *Escherichia coli* 16 S Ribosomal RNA. I. Fitting the RNA to a 3D Electron Microscopic Map at 20 Å," *J. Mol. Biol.* 271:524–544.

Oehler, R. et al. (1997). "Interaction of Tetracycline with RNA: Photoincorporation into Ribosomal RNA of *Escherichia coli,*" *Nucleic Acids Res* 25(6):1219–1224.

Ogle, J. M. et al. (2001). "Recognition of Cognate Transfer RNA by the 30S Ribosomal Subunit," *Science* 292:897–902.

Pape, T. et al. (2000). "Conformational Switch in the Decoding Region of 16s rRNA During Aminoacyl–tRNA Selection on the Ribosome," *Nat. Struct. Biol.* 7(2):104–107.

Pinard, R. et al. (1993). "The 5' Proximal Helix of 16S rRNA is Involved in the Binding of Streptomycin to the Ribosome", *FASEB J.* 7:173–176.

Pioletti, M. et al. (2001). "Crystal Structures of Complexes of the Small Ribosomal Subunit with Tetracycline, Edeine and IF3," *EMBO Journal* 20(8):1829–1839.

Powers, T. and Noller, H. F. (1991). "A Functional Pseudoknot in 16S Ribosomal RNA," *EMBO J.* 10:2203–2214.

Ross, J. I. et al. (1998). "16S rRNA Mutation Associated with Tetrycycline Resistance in a Gram–Positive Bacterium," *Antimicob Agent Chemother* 42(7):1702–1705.

Schluenzen et al. (2000). "Structure of Functionally Activated Small ribosomal Subunit at 3.3Å Resolution," *Cell* 102:615–623.

Spahn, C. M. and Prescott, C. D. (1996). "Throwing a Spanner in the Works: Antibiotics and the Translation Apparatus," *J. Mol Med* 74:423–439.

Spangler, E. A. and Blackburn, E. H. (1985). "The Nucleotide Sequence of the 17S Ribosomal RNA Gene of Tetrahymena Thermophila and the Identification of Point Mutations Resulting in Resistance to the Antibiotics Paromomycin and Hygromycin," *J. Biol. Chem.* 260(10):6334–6340.

Tejedor, R. et al. (1985). "Photoaffinity Labeling of the Pactamycin Binding Site on Eubacterial Ribosomes," *Biochemistry* 24:3667–3672.

Timms, A. R. et al. (1992). "Mutant Sequences in the rpsL Gene of *Escherichia coli* B/r: Mechanistic Implications for Spontaneous and Ultraviolet Light Mutagenesis," *Mol Gen Genet* 232:89–96.

Timms, A. R. and Bridges, B.A. (1993). "Double, Independent Mutational Events in the rpsL Gene of *Escherichia coli*: and Example of Hypermutability," *Mol. Microbiol.* 9(2):335–342.

Tubulekas, I. et al. (1991). "Mutant Ribosomes Can Generate Dominant Kirromycin Resistance," *J. Bacteriol.* 173(12):3635–3643.

VanLoock, M. S. et al. "Major Groove Binding of the tRNA/mRNA Complex to the 16S Ribosomal RNA Decoding Site," *J. Mol. Biol.* 285:2069–2078.

Woodcock, J. et al. (1991). "Interaction of Antibiotics with A– and P–Site–Specific Bases in 16S Ribosomal RNA," *EMBO J.* 10:2099–3103.

Yoshizawa, S. et al. (1999). "Recognition of the Codon–Anticodon Helix by Ribosomal RNA," *Science* 285:1722–1725.

Zierhut, G. et al. (1979). "Comparative Analysis of the Effect of Aminoglycosides on Bacterial Protein Synthesis In Vitro," *Eur. J. Biochem.* 98:577–583.

Walter, W. P. et al. (1998). "Virtual Screening—An Overview," *Drug Delivery Today* 3(4):160–178.

Wimberly, B. T. (2000). "Structure of the 30S Ribosomal Subunit," *Nature* 407:327–339.

Wittmann–Liebold, B. and Greuer, B. (1978). "The Primary Structure of Protein S5 from the Small Subunit of the *Escherichia coli* Ribosome," *FEBS Letters* 95(1):91–98.

Wu, H. et al. (1993). "The Binding Site for Ribosomal Protein S8 in 16S rRNA and spc mRNA from *Escherichia coli*: Minimum Structural Requirements and the Effects of Single Bulged Bases on S8–RNA Interaction," *Nucleic Acids Res.* 22:1687–1695.

Yonath, A. et al. (1998). "Crystallographic Studies on the Ribosome, A Large Macromolecular Assembly Exhibiting Severe Nonisomorphism, Extreme Beam Sensitivity and No Internal Symmetry," *Acta Cryst.* A54: 945–955.

Yonath, A. et al. "Characterization of Crystals of Small Ribosomal Subunits," *J. Mol. Biol.* 203:831–834 (1988).

Yusupov, M. M. et al. (1988). "A New Crystalline Form of 30S Ribosomal Subunits from Thermus Thermophilus," *FEBS Letters* 238:113–115.

Abrahams, J. P. (1997). "Bias Reduction in Phase Refinement by Modified Interference Functions: Introducing the Gamma Correction," *Acta Cryst* D53:371–376.

Agalarov, S. C. et al. (2000). "Structure of the S15, S6, S18–rRNA Complex: Assembly of the 30S Ribosome Central Domain," *Science* 288:107–112.

Allard, P. et al. (2000)."Another Piece of the Ribosome: Solution Structure of S16 and Its Location in the 30S Subunit," *Structure* 8(8): 875–882.

Blundell, T. L. et al. (1976). *Protein Crystallography*. Academic Press: New York, NY.,and Johnson, L. N., eds. pp. ix–xiv (Table of Contents Only).

Brünger, A. T. et al. (1998). "Crystallography and NMR System: A New Software Suite for Macromolecular Structure Determination," *Acta Cryst.* D54:905–921.

Cate, J. H. et al. (1999). "X–Ray Crystal Structures of 70S Ribosome Functional Complexes," *Science* 285:2095–2104.

Clemons, Jr. W. M. et al. (1999). "Structure of a Bacterial 30S Ribosomal Subunit at 5.5 Å Resolution," *Nature* 400:833–840.

Collaborative Computational Project 4 (1994). "The CCP4 Suite: Programs for Protein Crystallography," *Acta Cryst.* D50:760–763.

Cowtan, K. and Main, P. (1998). "Miscellaneous Algorithms for Density Modification", *Aca Crytallogr D. Biol. Crystallogr* 54:487–493.

Davies, C. et al. (1998). "The Crystal Structural of Ribosomal Protein S4 Reveals a Two–Domain Molecule with an Extensive RNA–Binding Surface: One Domain Shows Structural Homology to the ETS DNA–Binding Motif," *EMBO. J.* 17:4545–4558.

Dunbrack, R. L. et al (1997). "Meeting Review: the Second Meeting on the Critical Assesment of Techniques for Protein Structure Prediction (CASP2), Asilomar, California, Dec. 13–16, 1996," *Folding and Design* 2:R27–R42.

Gabashvili, I. S. et al. (1999). "Major Rearrangements in the 70S Ribosomal 3D Structure Caused by a Conformational Switch in 16S Ribosomal RNA," *EMBO J.* 18(22):6501–6507.

Garrett, R. A. et al., eds. (2000). *The Ribosome. Structure, Function, Antibiotics and Cellular Interactions*. ASM Press: Washington DC., pp. v–viii (Table of Contents Only).

Glotz, C. et al. (1987). "Three Dimensional Crystals of Ribosomes and Their Subunits from EU– and Archaebacteria," *Biochem Int.* 15(5):953–960.

Golden, B. L. et al. (1993). "Ribosomal Protein S17 Characterization of the Three–Dimensional Structure by 1H– and 15N–NMR," *Biochemistry* 32:12812–12820.

Goodford, P. J. (1985). "A Computational Procedure for Determining Energetically Favorable Binding Sites on Biologically Important Macromolecules," *J. Med. Chem.* 28:849–857.

Greer, J. et al. (1994). "Application of the Three–Dimensional Structures of Protein Target Molecules in Structure–Based Drug Design," *J. of Medicinal Chemistry* 37:1035–1054.

Hartmann, R. K. and Erdmann, V. A. (1989). "Thermus Thermophilus 16S rRNA is Transcribed from an Isolated Transcription Unit," *J. Bacteriol.* 171(6):2933–2941.

Helgstrand, M. et al. (1999). "Solution Structure of the Ribosomal Protein S19 from Thermus Thermophilus," *J. Mol. Biol.* 292:1071–1081.

Hüttenhofer, A. and Noller, H. F. (1992). "Hydroxyl Radical Cleavage of tRNA in the Ribosomal P–Site," *Proc. Nat.l Acad. Sci. USA* 89:7851–7855.

Jack, A. et al. (1976). "Crystallographic Refinement of Yeast Phenylalanine Transfer RNA at 2–5A Resolution," *J. Mol. Biol* 108:619–649.

Jones, T. A. et al. (1991). "Improved Methods for Building Protein Models in Electron Density Maps and the Location of Errors in These Models," *Acta. Cryt. A*47: 110–119.

Jones, T. A. & Kjeldgaard, M. (1997). "Electron–Density Map Interpretation," *Meth. Enzymol.* 277:173–207.

Lodmell, J. S. and Dahlberg, A. E. (1997). "A Conformational Switch in *Escherichia coli* 16S Ribosomal RNA During Decoding of Messenger RNA," *Science* 277:1262–1267.

Markus, M. A. et al. (1998). "The Solution Structure of Robosomal Protein S4 Delta41 Reveals Two Subdomains and a Positively Charged Surface that May Interact with RNA," *EMBO J.* 17(16):4559–4571.

Moazed, D. and Noller, H. F. (1990). "Binding of tRNA to the Ribosomal A and P–sites Protects Two Distinct Sets of Nucleotides in 16 S rRNA," *J. Mol. Biol.* 211:135–145.

Mougel, M. et al. (1993). "Minimal 16S rRNA Binding Site and Role of Conserved Nucleotides in *Escherichia coli* Ribosomal Protein S8 Recognition ," *Eur. J. Biochem.* 215:787–792.

Nowotny, V. and Nierhaus, K. H. (1988). "Assembly of the 30S Subunit from *Escherichia coli* Ribosomes Occurs via Two Assembly Domains which Are Initiated by S4 and S7," *Biochemistry* 27:7051–7055.

Prince, J. B. et al. (1982). "Covalent Crosslinking of tRNA 1Val to 16S RNA at the Ribosomal P–Site: Identification of Crosslinked Residues," *Proc. Natl. Acad. Sci. USA* 79:5450–5454.

Rich, A. and RajBhandary, U.L. (1976). "Transfer RNA: Molecular Structure, Sequence, and Properties," *In Annual Reviews of Biochemistry*. E.E. Snell et al., eds. Annual Reviews,Inc.: Palo Alto, CA., pp. 805–860.

Rose, S. J. III et al. (1983). "Binding of Yeast tRNAPhe Anticodon Arm to *Escherichia coli* 30S Ribosomes," *J. Mol. Biol.* 167:103–117.

Tanaka, I. et al. (1998). "Matching the Crystallographic Structure of Ribosomal Protein S7 to a Three–Dimensional Model of the 16S Ribosomal RNA," *RNA* 4:542–550.

Terwilliger, T. C.and Berendzen, J. (1999). "Automated MAD and MIR Structure Determination," *Acta Cryst.* D55:849–861.

Tocilj, A. et al. (1999). "The Small Ribosomal Subunit from Thermus Thermophilus at 4.5 Resolution: pattern Fittings and the Identification of a Functional Site," *Proc. Natl. Acad. Sci. USA* 96:14252–14257.

Trakhanov, S. D. et al. (1987). "Crytallization of 70S Ribosomes and 30S Ribosomal Subunits from Thermus Thermophilus," *FEBS Letters* 220:319–322.

Urlaub, H. et al. (1997). "Identification and Sequence Analysis of Contact Sites Between Ribosomal Proteins and rRNA in *Escherichia coli* 30 S Subunits by a New Approach Using Matrix–Assisted Laser Desorption/Ionization–Mass Spectrometry Combined with N–Terminal Microsequencing," *J. Biol. Chem.* 272:14547–14555.

van Acken, U. (1975). "Proteinchemical Studies on Ribosomal Proteins S4 and S12 from Ram (Ribosomal Ambiguity) Mutants of *Escherichia coli,*" *Mol Gen Genet.* 140:61–68.

von Ahsen, U. and Noller, H. F. (1995). "Identification of Bases in 16S rRNA Essential for tRNA Binding at the 30S Ribosomal P–Site," *Science* 267:234–237.

von Böhlen, K. et al. (1991). "Characterization and Preliminary Attempts for Derivatization of Crystals of Large Ribosomal Subunits form Haloarcula Marismortui Diffracting to 3 Å Resolution," *J. Mol. Biol.* 222:11–15.

* cited by examiner

CRYSTAL STRUCTURE OF THE 30S RIBOSOME

STATEMENT OF RIGHTS TO INVENTIONS MADE UNDER FEDERALLY SPONSORED RESEARCH

This invention was made in part with U.S. Government support under NIH grant GM 44973 awarded by the PHS. The U.S. Government has certain rights in the invention.

CROSS REFERENCE TO RELATED APPLICATION

This application claims priority from United Kingdom (U.K.) applications 0017376.5 filed Jul. 14, 2000, 0022943.5 filed Sep. 19, 2000 the contents of which are incorporated herein by reference.

DESCRIPTION OF ACCOMPANYING CD-ROM (37 C.F.R. §§1.52 & 1.58)

Tables 1A and 1B referred to herein (also referred herein as Table 1) are filed herewith on CD-ROM in accordance with 37 C.F.R. §§1.52 and 1.58. Two identical copies (marked "Copy 1" and "Copy 2") of said CD-ROM, both of which contain Tables 1A and 1B, are submitted herewith, for a total of two CD-ROM discs submitted. Table 1A is recorded on said CD-ROM discs as "Table 1A.txt" created Jul. 12, 2001, size 3,952 KB. Table 1B is recorded on said CD-ROM discs as "Table 1B.txt" created on Jul. 12, 2001, size 4,168 KB.

The contents of the files contained on the CD-ROM discs submitted with this application are hereby incorporated by reference into the specification.

FIELD OF THE INVENTION

The present invention relates to the provision of a high resolution crystal structure of the prokaryotic 30S ribosome subunit, and the use of this structure in drug discovery.

BACKGROUND OF THE INVENTION

The wealth of information made available through efforts in structural genomics and advances in computation has allowed structure-based drug design to emerge as a valuable tool in medicinal chemistry. In the past combinatorial chemistry, coupled with high-throughput approaches, shifted attention away from the more structure-based methods. Large-scale determination of protein structures is reversing the drug discovery process by starting with the protein structure and using it to identify and design new ligands. It is the integration of structure-based methods, virtual screening, and combinatorial chemistry that will provide the basis for more efficient drug design in the future, significantly reducing the time of the design cycle and the cost per marketed drug. Significant advances have already been made in AIDS, arthritis and cancer and in the treatment of hypertension (e.g. captopril).

Translation of the genetic code occurs on the ribosome, a large nucleoprotein complex that consists of two subunits. In bacteria, the two subunits are denoted 30S and 50S. The 50S subunit contains the catalytic site of peptidyl transferase activity, while the 30S subunit plays a crucial role in decoding messenger RNA. Protein synthesis is a complex, multistep process that requires several extrinsic GTP-hydrolysing protein factors during each of the main stages of initiation, elongation and termination. Despite several decades of work, the molecular details of the process are poorly understood, and the elucidation of the mechanism of translation is one of the fundamental problems in molecular biology today. A recent collection of articles summarizes the state of understanding of the field [1].

A contribution to this problem was made by Yonath and coworkers, who after nearly a decade of work showed that structures as large as the 50S ribosomal subunit would form crystals that diffract beyond 3 Å resolution [2]. Originally, it was not clear that phase information from such a large asymmetric unit could be obtained to high resolution, but the development of bright, tuneable synchrotron radiation sources, large and accurate area detectors, vastly improved crystallographic computing, and the advent of cryocrystallography have all contributed to making structural studies of the ribosome more tractable. In our work, the use of anomalous scattering from the LIII edges of lanthanides and osmium has also played a critical role in obtaining phases.

The 30S ribosomal subunit (hereafter referred to as 30S) from *Thermus thermophilus* was originally crystallized by Trakhanov et al. in 2-methyl-2,4-pentanediol (MPD) [3] and soon afterwards by Yonath and coworkers in a mixture of ethyl-butanol and ethanol [4]. Subsequent work by both groups showed that the MPD crystal form diffracted to about 9–12 Å resolution [5, 6]. The diffraction limit of these crystals did not improve beyond 7 Å resolution for almost a decade, but more recently both Yonath and coworkers [7, 8] and we [9] obtained crystals of the MPD form that exhibit significantly improved diffraction. However, unlike the crystals obtained by the Yonath group [6], our crystals do not require soaking in tungsten clusters or heat treatment in order to obtain high resolution diffraction.

We have previously described the structure of the 30S at 5.5 Å resolution [9]. We were able to place all seven proteins whose structures were known at the time, infer the structure of protein S20 to be a three-helix bundle, trace the fold of an entire domain of 16S RNA, and identify a long RNA helix at the interface that contains the decoding site of the 30S. Proteins S5 and S7 were also placed in electron density maps of the 30S obtained by Yonath and coworkers.

The 30S ribosomal subunit is a major target for antibiotics. The ribosome is a useful target for antibiotics since the structure of the 30S is widely conserved between prokaryotes, allowing for broad spectrum antibiotics. However, resistance to current antibiotics is currently a major problem in the field of medicine. There are presently very few new antibiotics available which can be used to treat the highly resistant strains of bacteria such as MRSA (methicilin resistant *Staphylococcus aureus*) which are becoming increasingly widespread.

Understanding the interaction of antibiotics with the ribosome at the molecular level is important for two reasons. Firstly, antibiotics act by interfering with various aspects of ribosome function. Thus understanding their interaction will help shed light on mechanisms involved in translation. Secondly, a detailed knowledge of antibiotic interactions with the ribosome could aid the development of new drugs against increasingly resistant strains of bacteria. Although antibiotics were characterized several decades ago, a detailed knowledge of their mechanism will in general require a three-dimensional structure of their complex with the ribosome.

The low (greater than 3 Å) resolution crystal structures described above do not provide sufficiently detailed resolution for useful modelling of the crystal structure of the 30S and there is thus a need for a high resolution structure which can be useful in the development of novel therapeutics.

All references cited herein, including patent applications and publications, are incorporated by reference in their entirety.

SUMMARY OF THE INVENTION

We have now solved and refined the structure of the 30S at 3 Å resolution. The structure contains all of the ordered regions of 16S RNA and 20 associated proteins, and contains over 99% of the RNA sequence and 95% of the protein sequences, with the missing parts being exclusively at the termini of RNA or polypeptide chains. Here we describe the overall architecture and the main structural features of the 30S subunit.

The refined atomic resolution model of the 30S presented here allows the interpretation of a vast amount of biochemical data on its function in precise structural terms. The structure will also serve as a basis for the interpretation in molecular terms of lower resolution models of various functional states by electron-microscopy or x-ray crystallography. The 30S structure will help produce testable models for various aspects of ribosome function.

In a first aspect, the present invention provides a crystal of the *Thermus thermophilus* 30S subunit having a tetragonal space group $P4_12_12$ with unit cell dimensions of a=401.375 Å, b=401.375 Å, c=175.887 Å, or more generally about a=401.4 Å, b=401.4 Å, c=175.9 Å, but more preferably a=401.4±about 4.0 Å, b=401.4±about 4.0 Å, c=175.9±about 5.0 Å. An advantageous feature of the structure is that it diffracts beyond 3 Å resolution. Another feature of the structure is that it was obtained in a method which did not involve soaking crystals in heavy atom (e.g. tungsten or tantalum) clusters or heat activation. Furthermore, it is specifically of the 885–888/910–912 base pairing confirmation of 16S RNA. These features, both singly and in combination all contribute to features of the invention which are advantageous.

In a second aspect, the invention also provides a crystal of 30S having the three dimensional atomic coordinates of the 30S ribosome. Table 1A provides a set of atomic coordinates of the 30S ribosome. Table 1B provides a set based upon the coordinates of Table 1A but which have been refined further from our data. Reference herein to "Table 1" is a reference to either of Table 1A or 1B (or where the context permits, both; i.e., reference to "Table 1" refers to Table 1A and/or Table 1B). Thus, for example, where it is stated that the invention refers to computer readable media with "atomic coordinate data according to Table 1 recorded thereon", this means that the media has either the data of Table 1A, or the data of Table 1B, or both, recorded thereon.

We have also observed that 30S crystals do not contain the S1 subunit protein. In our studies, we have found that by selectively removing this protein prior to crystallization, we have been able to obtain the improved resolution described herein. Although the atomic co-ordinates provided in Table 1 below allows those of skill in the art to bypass the need to undertake the crystallization of the 30S, this crystallization method nonetheless forms a further aspect of the invention.

Accordingly, there is provided a method for crystallizing a 30S subunit to obtain a high resolution structure of a 30S subunit, which method comprises providing a 30S subunit, selectively removing the S1 subunit therefrom and crystallizing the 30S.

In a further aspect, the present invention provides a method for identifying a potential inhibitor of the 30S comprising the steps of:

a. employing a three-dimensional structure of 30S, or at least one sub-domain thereof, to characterise at least one active site, the three-dimensional structure being defined by atomic coordinate data according to Table 1; and b. identifying the potential inhibitor by designing or selecting a compound for interaction with the active site.

In a further aspect, the present invention provides computer readable media with either (a) atomic coordinate data according to Table 1 recorded thereon, said data defining the three-dimensional structure of 30S or at least one sub-domain thereof, or (b) structure factor data for 30S recorded thereon, the structure factor data being derivable from the atomic coordinate data of Table 1.

DESCRIPTION OF ACCOMPANYING CD-ROM (37 C.F.R. §§1.52 & 1.58)

Figure 1:
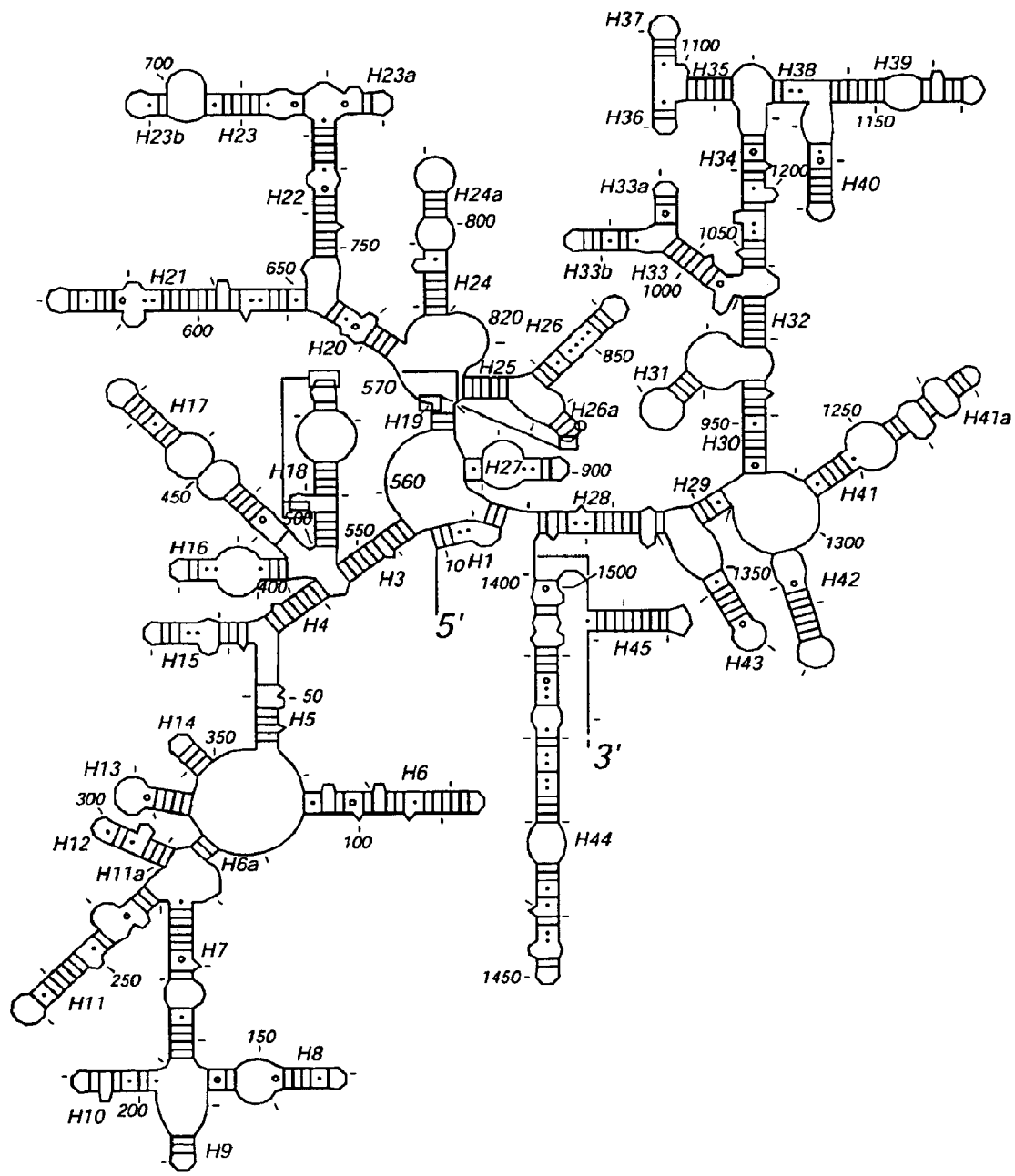
FIG. 1 shows the secondary structure of the 30S ribosome.

Tables 1A and 1B referred to herein (also referred herein as Table 1) are filed herewith on CD-ROM in accordance with 37 C.F.R. §§1.52 and 1.58. Two identical copies (marked "Copy 1" and "Copy 2") of said CD-ROM, both of which contain Tables 1A and 1B, are submitted herewith, for a total of two CD-ROM discs submitted. Table 1A is recorded on said CD-ROM discs as "Table 1A.txt" created Jul. 12, 2001, size 3,952 KB. Table 1B is recorded on said CD-ROM discs as "Table 1B.txt" created on Jul. 12, 2001, size 4,168 KB.

The contents of the files contained on the CD-ROM discs submitted with this application are hereby incorporated by reference into the specification.

DETAILED DESCRIPTION OF THE INVENTION

Definitions

"A", "an", "the" and the like, unless otherwise indicated include plural forms.

The term "sub-domain" includes any one or more of the following:

(a) an element selected from the following:

at least one complete element of secondary structure, i.e. an alpha helix or a beta sheet, or RNA helix, as described in the detailed description below;

a group of two or more such elements which interact with each other;

at least one subunit protein;

a subgroup of subunit proteins, for example a group which includes two or more proteins which are found to interact with each other;

any of the above, when the protein(s) or element(s) thereof is used in conjunction with all or part of the 16S RNA structure associated with said element(s) or protein(s);

(b) a space of volume defining a region around any one particular atom of interest (e.g. an atom involved in binding to an antibiotic), the volume being less than the total volume of the tetragonal space of the complete crystal. For example, the coordinates of atoms in a volume of from about 500 to about 15,000 $Å^3$ may be selected and used for the present invention. Such a space may be a sphere having a diameter of from about 10 Å to about 30 Å, centred around a point of interest; and (c) a collection of at least about 10, e.g. at least about 25 such as at least about 50, more preferably at least about 100, even more preferably at least about 500 atoms and most preferably at least about 1000 atoms defined by the coordinates of Table 1, wherein at least 2 of said atoms, and preferably at least about 50% of said atoms of the collection are located within about 50 Å of each other.

An "active site" of the 30S is any part of this structure involved in tRNA or mRNA binding, factor binding or translocation. This includes regions responsible for binding initiation factors, elongation factor G or release factors, regions which are target sites for regulation by co-factors, phosphorylation or acetylation, and regions responsible for interaction with the 50S ribosome. In also includes regions which change conformation during translocation or protein synthesis, particularly one or more of the 16S RNA helixes 18, 27, 34 and 44.

Particular regions of the 30S include antibiotic binding regions. Other regions include the three tRNA binding sites, i.e. the aminoacyl (A), peptidyl (P) and exit (E) sites. Other active sites are those which undergo movement during translocation of tRNAs from the A to P sites and the P to E sites. Regions further include any one of the subunit proteins S2 to S20 and THX, including any of the individually identified subunit proteins in the accompanying examples.

By "fitting", is meant determining by automatic or semi-automatic means, interactions between one or more atoms of an potential inhibitor molecule and one or more atoms or binding sites of the 30S, and calculating the extent to which such interactions are stable. Various computer-based methods for fitting are described further herein.

By "root mean square deviation" we mean the square root of the arithmetic mean of the squares of the deviations from the mean.

"Computer readable media" refers to any media which can be read and accessed directly by a computer. Such media include, but are not limited to: magnetic storage media such as floppy discs, hard disc storage medium and magnetic tape; optical storage media such as optical discs or CD-ROM; electrical storage media such as RAM and ROM; and hybrids of these categories such as magnetic/optical storage media.

A "computer system" refers to the hardware means, software means and data storage means used to analyse the atomic coordinate data of the present invention. The minimum hardware means of the computer-based systems of the present invention comprises a central processing unit (CPU), input means, output means and data storage means. Desirably a monitor is provided to visualise structure data. The data storage means may be RAM or means for accessing computer readable media of the invention. Examples of such systems are microcomputer workstations available from Silicon Graphics Incorporated and Sun Microsystems running Unix based, Windows NT or IBM OS/2 operating systems.

A "ligand" is any chemical moiety (organic or inorganic) that binds or interacts, generally but not necessarily specifically, to or with another chemical entity.

Table 1.

The coordinates of Table 1 provide a measure of atomic location in Angstroms, to a third decimal place. In order to use the information in these Tables for the purposes described herein as being aspects of the present invention, these coordinates may be varied by up to about ±1.0, such as by up to about ±0.7, preferably no more than up to about ±0.5 Angstroms, without departing from the scope of the invention.

Furthermore, varying the relative atomic positions of the atoms of the structure so that the root mean square deviation of the 16S RNA or S2–S20 protein backbone atoms is less than about 1.5 Å (preferably less than about 1.0 Å and more preferably less than about 0.5 Å) when superimposed on the coordinates provided in Table 1 for these structures, will generally result in a structure which is substantially the same as the structure of Table 1 in terms of both its structural characteristics and potency for structure-based drug design of 30S ligands.

Thus for the purposes described herein as being aspects of the present invention, it is within the scope of the invention if: the Table 1 coordinates are transposed to a different origin and/or axes; the relative atomic positions of the atoms of the structure are varied so that the root mean square deviation of conserved residue backbone atoms is less than about 1.5 Å (preferably less than about 1.0 Å and more preferably less than about 0.5 Å) when superimposed on the coordinates provided in Table 1 for the conserved residue backbone atoms; and/or the number and/or positions of water molecules is varied. Reference herein to the use of the coordinates of Table 1 thus includes the use of coordinates in which one or more individual values of the Table are varied in this way.

Table 1 includes coordinates of two zinc ions, together with 202 other ions which are not identified, which, while not wishing to be bound by any one theory, are believed to be selected from cobalt and magnesium. Some or all of these ions may optionally be discarded from Table 1 when using the data. The table also lists the coordinates of a 26 amino acid peptide, Thx, as well as a 6 nucleotide fragment of mRNA, NNNUCU, designated as molecule X. Both the coordinates of both these molecules may likewise optionally be discarded, i.e. so that the coordinates of the 16S RNA and the proteins S2 to S20 alone are modelled and used in applications of the invention.

There are a few N- or C-terminal sequences of the S2 to S20 proteins which were not resolved in the structure of Table 1, together with a some of the 5' and 3' residues of the 16S RNA. These are not essential for the purposes of the present invention, but are listed in Table 2 for completeness. Those of skill in the art may, if desired, wish to adapt the structures provided by the coordinate of Table 1 by modelling in one or more of the amino acids or nucleotides of Table 2.

This methodology provides those of skill in the art a means to provide 30S crystals of *T. thermophilus*. The conservation of ribosome structure, particularly regions of structure essential for function, between prokaryotes, for example prokaryotes which are human pathogens, such as *Staphylococcus* spp, and the like, allows the structure herein to be useful in the provision of anti-bacterial agents in general. Thus, the structure may be used to solve 30S subunits by the technique of molecular replacement. In such a method, x-ray diffraction data are obtained from crystals of a 30S subunit from another species, e.g. a species of a bacteria pathogenic to humans. The coordinates of Table 1 may be used to find the orientation of the unknown molecule in the crystal, and electron density maps calculated. These maps can then be interpreted with the sequence of the species in question, and the coordinates of our 30S structure can be used to help and speed interpretation. In this way, the structure of our 30S facilitates the determination of structures of 30S subunits and whole ribosomes from other organisms.

Accordingly, the invention provides a method for the determination of the structure of a bacterial 30S from a species other than *T. thermophilus* which method comprises:

(a) crystallising the 30S of said species to obtain a crystal;
(b) performing X-ray crystallography on said crystal to obtain X-ray diffraction data;
(c) providing the structure data of Table 1; and
(d) using molecular replacement to calculate an electron density map of the 30S.

In such a method the 30S may be prepared by removal of the S1 subunit, as described herein.

The electron density map obtained may then be used to calculate the atomic coordinate data of the 30S. The atomic coordinate data thus obtained may be used to for the design and analysis of new and specific ligands for 30S as described herein.

The 30S Crystal Structure

The high resolution structure provided herein provides a crystal with unit cell dimensions which are provided in the accompanying table to 3 decimal places, i.e. a=b=401.375, c=175.887 Å. However, those of skill in the art wishing to reproduce the crystallization described herein and obtain such crystals will appreciate that a degree of experimental variability and error will mean that crystals of the invention will be obtained with a unit cell dimension within, but not exactly corresponding to, this size. Thus crystals of the invention may generally be defined as having unit cell dimensions of a=401.4±about 4.0 Å, b=401.4±about 4.0 Å, c=175.9±about 5.0 Å, preferably a=401.4±about 1.0 Å, b=401.4±about 1.0 Å, c=175.9±about 2.0 Å, preferably a=401.4±about 0.7 Å, b=401.4±about 0.7 Å, c=175.9±about 1.4 Å, and more preferably a=401.4±about 0.2 Å, b=401.4±about 0.2 Å, c=175.9±about 0.4 Å. These unit cell sizes are believed to define a novel and more highly resolved unit cell size than has previously been possible in the art.

Production of Crystals.

To obtain crystals according to the present invention, we have found that selective removal of the S1 subunit protein is advantageous. A suitable method for the selective removal of the S1 subunit protein is by the use of a hydrophobic interaction chromatography column (poros-ET). 30S ribosomal subunits lacking the S1 subunit may suitably be separated from those containing the S1 subunit by running a column using a reverse ammonium sulfate gradient from 1.5M to 0.5M, with 20 mM Hepes, pH 7.5, and 10 mM acetate. The 30S subunits lacking S1 are eluted first, giving the first major peak. During elution of the 30S peak the ammonium sulfate concentration is maintained at a constant level. Once the 30S peak has eluted the ammonium sulfate concentration is then further reduced to elute the 30S+S1 fraction.

An alternative method for the selective removal of the S1 subunit protein is by preparative gel electrophoresis. Gel electrophoresis may suitably be carried out by first preparing and mixing a 3% acrylamide, 0.5% agarose cylindrical gel, and pouring this gel into a BioRad Prep Cell. 30S ribosomal subunits are then loaded onto the gel and continuously eluted as they emerge form the other end of the gel. The 30S fraction lacking the S1 subunit comes off first, giving the first major peak. The 30S+S1 fraction gives the trailing peak (or shoulder) and can be discarded.

Once the S1 is removed, the crystals may be formed, using suitable conditions. These include the use of 13–17% v/v methyl-2,4-pentanediol in the presence of 200–300 (e.g. about 250) mM KCl, 50–100 (e.g. about 75) mM ammonium chloride, 15–30 (e.g. about 15 or about 25) mM $MgCl_2$ at a pH of 6.0–7.5 (e.g about pH 6.3–6.7 such as pH 6.5) in 50–150 (e.g. about 100) mM sodium or potassium cacodylate or MES (2-(N-morpholino)ethane sulphonic acid).

In a particular aspect, the conditions may comprise the use of 250 mM KCl, 75 mM $NH_4Cl$, 25 mM $MgCl_2$, 6 mM 2-mercaptoethanol in 0.1 M potassium cacodylate or 0.1 M MES (2-N-morpholino-ethanesulfonic acid) at pH 6.5 with 13–17% MPD as the precipitant.

The crystals may be grown by any suitable method known as such to those of skill in the art. Suitably, the crystals may be grown over a period of 4–8 weeks at about 4° C. The structure of the crystals so obtained may be resolved, and crystals which resolve to a resolution of at least about 3 Å selected. Crystals which resolve to a resolution of at least about 3 Å obtainable by such a method are a further aspect of the invention.

Uses of Structural Data of Table 1.

The determination of the three-dimensional structure of 30S provides a basis for the design of new and specific ligands for 30S. For example, knowing the three-dimensional structure of 30S, computer modelling programs may be used to design different molecules expected to interact with possible or confirmed active sites, such as binding sites or other structural or functional features of 30S.

The high resolution model of the 30S provided by Table 1 may be used to examine and determine the binding of antibiotics known to target this ribosome subunit. Such antibiotics include paromomycin, streptomycin, spectinomycin, tetracycline, pactamycin and hygromycin B.

A candidate ligand, particularly but not necessarily one which acts as an inhibitor molecule, may be any available compound. A number of commercial sources of libraries of compound structures are available, for example the Cambridge Structural Database. Such libraries may be used to allow computer-based high throughput screening of many compounds in order to identify those with potential to interact with the active site of a ribosome.

More specifically, a potential ligand capable of modulating 30S activity can be examined through the use of computer modelling using a docking program such as GRAM, DOCK, or AUTODOCK (see Walters et al., *Drug Discovery Today*, Vol.3, No.4, (1998), 160–178, and Dunbrack et al., *Folding and Design*, 2, (1997), 27–42) to identify potential ligands of 30S. This procedure can include computer fitting of potential ligands to 30S or a subdomain thereof to ascertain how well the shape and the chemical structure of the potential ligand will bind to the enzyme.

Also computer-assisted, manual examination of the active site structure of 30S may be performed. The use of programs such as GRID (Goodford, *J. Med. Chem.*, 28, (1985), 849–857)—a program that determines probable interaction sites between molecules with various functional groups and the enzyme surface—may also be used to analyse the active site to predict partial structures of ligands for the site.

Computer programs can be employed to estimate the attraction, repulsion, and steric hindrance of the two binding partners (e.g. the 30S and a potential ligand). Generally the tighter the fit, the fewer the steric hindrances, and the greater the attractive forces, the more potent the potential ligand since these properties are consistent with a tighter binding constant. Furthermore, the more specificity in the design of a potential ligand, the more likely it is that the ligand will not interact with other proteins as well. This will tend to minimise potential side-effects due to unwanted interactions with other proteins.

Having designed or selected possible binding ligands, these can then be screened for activity. Consequently, the method preferably further comprises the further steps of:
  obtaining or synthesising the potential ligand; and
  contacting the potential ligand with 30S to determine the ability of the potential ligand to interact with 30S.

More preferably, in latter step the potential ligand is contacted with 30S under conditions to determine its function, for example in a cell free translation system. Such conditions (including cell free translation systems) are known in the art.

Instead of, or in addition to, performing such an assay, the method may comprise the further steps of:

obtaining or synthesising said potential ligand;

forming a complex of 30S and said potential ligand; and analysing said complex by X-ray crystallography to determine the ability of said potential ligand to interact with 30S. Detailed structural information can then be obtained about the binding of the potential ligand to 30S, and in the light of this information adjustments can be made to the structure or functionality of the potential ligand, e.g. to improve binding to the active site. These steps may be repeated and re-repeated as necessary.

Another aspect of the invention includes a compound which is identified as an ligand of 30S by the method of the above aspects of the invention.

The present high resolution structure of 30S provides a means to determine the location of binding of antibiotics, as well as the interactions at the location(s) between 30S and the antibiotic. Such antibiotics include paromomycin, streptomycin spectinomycin, tetracycline, pactamycin and hygromycin B. The high resolution structure of Table 1 may be used to model the binding to 30S of these, other antibiotics and other ligands. Thus in another aspect, the invention provides a method of analysing a 30S-ligand (wherein "ligand" includes, but is not limited to, an antibiotic) complex comprising the steps of (i) cocrystallising the 30S with the ligand or soaking the ligand into crystals of the 30S; (ii) collecting X-ray crystallographic diffraction data from the crystals of the 30S-ligand complex and (iii) using the three-dimensional structure of 30S of Table 1, or at least one sub-domain thereof, to generate a difference Fourier electron density map of the 30S-ligand; and (iv) modelling the ligand in the difference Fourier electron density.

Therefore, 30S-ligand complexes can be crystallised and analysed using X-ray diffraction methods, e.g. according to the approach described by Greer et al., *J. of Medicinal Chemistry*, Vol.37, (1994), 1035–1054, and difference Fourier electron density maps can be calculated based on X-ray diffraction patterns of soaked or co-crystallised 30S and the solved structure of uncomplexed 30S. These maps can then be used to determine the structure of the ligand bound to the 30S and/or changes the conformation of 30S.

Data obtained from a ligand bound to 30S may be used to improve the ligand, for example by adding or removing functional groups, substituting groups or altering its shape to obtain improved candidates, which may then be screened, solved in complex as described herein above, in an iterative process.

Electron density maps can be calculated using programs such as those from the CCP4 computing package (Collaborative Computational Project 4. The CCP4 Suite: Programs for Protein Crystallography, *Acta Crystallographica*, D50, (1994), 760–763.). For map visualisation and model building programs such as "O" (Jones et al.,*Acta Crystallograhy*, A47, (1991), 110–119) can be used.

By providing such computer readable media, the atomic coordinate data can be routinely accessed to model 30S or a sub-domain thereof. For example, RASMOL is a publicly available computer software package which allows access and analysis of atomic coordinate data for structure determination and/or rational drug design.

On the other hand, structure factor data, which are derivable from atomic coordinate data (see e.g. Blundell et al., in *Protein Crystallography*, Academic Press, New York, London and San Francisco, (1976)), are particularly useful for calculating, e.g., difference Fourier electron density maps.

In another aspect, the present invention provides systems, particularly a computer systems, intended to generate structures and/or perform rational drug design for 30S and/or 30S ligand complexes, the systems containing either (a) atomic coordinate data according to Table 1, said data defining the three-dimensional structure of 30S or at least one sub-domain thereof, or (b) structure factor data for 30S, said structure factor data being derivable from the atomic coordinate data of Table 1.

Mutant strains resistant to the action of these antibiotics can arise through mutation of a protein subunit of the 30S or through mutation or modification in the 16S RNA (e.g. 2'O-methylation), or modification (e.g. acetylation) of the antibiotic). The sites of mutations in some cases are known or can be identified. Where such sites are identified through, for example, primary sequence data, the invention provides a means to model the structure of the mutants.

There is thus provided a method which comprises providing the structure of the 30S ribosome of Table 1, changing one amino acid or nucleotide of said structure to provide a mutant 30S, and modelling the structure of the mutant 30S to provide a structure of the mutant. The mutant may be used in the manner described above for the wild type, e.g. stored in computer readable form, modelled to provide ligands, and the like. The modelling may be based upon the predicted behaviour of the atoms of the changed amino acid based upon its interaction with the surrounding atoms in the model provided herein.

This process may be iterative, e.g. to produce successive mutations into the 30S structure, for example 2, 3, 4, or 5 to 10 mutations or more.

Regions of 30S which may be subject to this aspect of the invention include but are not limited to those regions identified in the accompanying examples as regions of the 30S involved in ribosome function.

In a further aspect, the present invention provides a means to solve or interpret electron density maps of the whole 70S ribosome at low or high resolution, and thus solve the structure of the whole 70S ribosome.

In particular, the invention provides a method for the determination of the structure of a bacterial 70S ribosome which method comprises (a) crystallising the 70S of said species to obtain a crystal;

(b) performing X-ray crystallography on said crystal to obtain X-ray diffraction data;

(c) providing the structure data of Table 1; and (d) using molecular replacement to calculate an electron density map of the 70S.

The invention is illustrated, but not limited, below by the following examples and their accompanying Figure and Tables. In Table 1 there is shown in each row Atom number, element type, residue (amino acid, nucleotide, etc), number in molecule (for proteins N to C terminal direction, for nucleic acid 5' to 3' direction), X, Y and Z co-ordinates, occupancy, B factor ($Å^2$) and an identifier for the member of the 30S (e.g. for the subunits in the format "ASn" where A is an arbitrary letter, different for each member, S is the subunit and n is the subunit number; and for the 16S as "A16S").

Throughout the accompanying example, we use the numbering system for *E. coli* 16S RNA, as well as the standard helix numbering, denoted H1–H45, for the secondary structure elements [19] with some modifications as shown in FIG. 1. The most significant differences between the *E. coli* and T. thermophilus sequences are a shorter H6 and H10, and insertions in H9 and H33a. Any insertions in T. thermophilus relative to E. coli are indicated in the coordinates with an insertion letter after the nucleotide number, following the practice for tRNA.

EXAMPLE

Materials and Methods

Crystallization of the 30S.

Because we observed that the 30S crystals completely lacked ribosomal protein S1, care was taken to remove S1 selectively from the 30S prior to crystallization. Crystals were obtained in 13–17% MPD over a range of pH in the salt and magnesium conditions described by Trakhanov et al [3]. The crystals were largest and most reproducibly obtained at a pH of 6.5 in 0.1 M cacodylate or MES buffer. Crystals took approximately 6 weeks at 4° C. to grow to their maximum size. The largest crystals, which were required for high resolution data collection, grew to a size of 80–100× 80–100×200–300 microns. The activity of redissolved crystals in poly(U)-directed protein synthesis was comparable to that of freshly isolated 30S subunits.

Data Collection.

Crystals were transferred to 26% MPD by vapor diffusion in two steps over a period of 6 days. All crystals (except for those soaked in osmium hexammine or osmium pentammine) also contained 1 mM cobalt hexammine in the cryoprotectant. Crystals were flash-cooled by plunging into liquid nitrogen, and data collection was done in a cryostream at 90–100 K.

A large fraction of crystals was screened at beamlines 9.6 or 14.1 at the SRS at Daresbury Laboratories, using two short exposures at least 40 degrees apart. These crystals were then analyzed for diffraction limits, cell dimensions and mosaic spread. Only crystals of similar cell dimensions and with reasonable mosaic spread were used for data collection.

Potential derivatives were screened on beamlines X25 at the NSLS at Brookhaven National Laboratory and BM-14 at the ESRF (Grenoble). Data to about 4.5 Å were obtained from X25. High resolution data were collected at SBC ID-19 at the APS in Argonne National Laboratory, and ID14-4 at the ESRF. In all cases, derivative data were collected at the peak of the fluorescence at the LIII edge to maximize anomalous differences. At X25 and SBC ID-19, the kappa goniostat was used to rotate precisely about a mirror plane so that small anomalous differences could be measured accurately. Each crystal typically yielded 3–10 degrees of data. Data were integrated and scaled using HKL-2000 [10].

Structure Determination.

Previously determined phases at 5.5 Å [9] were used to locate heavy atom sites using anomalous difference Fourier maps. Initially, these sites were used for phasing to 3.35 Å using the program SOLVE [11], followed by density modification with SOLOMON [12], using the procedure implemented in SHARP [13]. Optimization of the various parameters in the procedure was required to obtain interpretable maps. The RNA and some of the proteins were built using the SOLVE maps. The sequence of Thermus thermophilus 16S RNA [ 14] was used for the structure. For proteins, a combination of previously published sequences and new ones from the Göttingen Thermus genome sequencing project were used. Improved maps were obtained by calculating experimental phases to 3.2 Å using SHARP followed by density modification and phase extension to 3.05 Å with DM [15]. The improved maps allowed us to build all the ordered parts of the structure. The model was built using O [16], and refined using the program CNS [17]. Maximum likelihood refinement was used, initially with both amplitudes and experimental phase probability distributions to 3.35 Å, and subsequently with amplitudes to 3.05 Å.

Results

The 30S subunit from Thermus thermophilus consists of a 1522 nucleotide 16S ribosomal RNA [14] and 21 associated proteins, of which 20 have known counterparts in E. coli. Protein S21 is not present in Thermus, and protein S1 has been removed from the 30S prior to our crystallization. In addition, a 26 residue peptide, Thx, is present in Thermus 30S subunits [18].

Experimentally phased maps clearly showed main chain density for RNA and protein, individual bases (which were often of sufficient quality to distinguish purines from pyrimidines), and large well-ordered side chains of proteins. These maps were used to build 16S RNA and the previously unknown proteins S2, S3, S9, S10, S11, S12, S13, S14 and Thx. In addition, regions that were disordered in isolated structures or had changed significantly were also built. This often consisted of significant portions of the N- and C-terminal tails of the proteins, sometimes including entire domains that were unfolded in isolation. Proteins with small cores and long loops, such as S16 and S17, had to be substantially rebuilt, since these loops were generally disordered in the solution NMR structures. Finally, the entire structure was rebuilt after an initial round of refinement. Our current model consists of nucleotides 5–1511 of Thermus thermophilus 16S RNA (corresponding to 5–1534 of E. coli 16S RNA) and all of the ordered regions of the associated 20 proteins. The current model has been refined against 3.05 Å data with a conventional R-factor of 0.213, a free R-factor of 0.256 and good geometry. For the proteins, 94% of the residues were in the core or allowed regions of the Ramachandran plot, 3.9% in the generously allowed region and 1.8% in the disallowed region.

16S RNA

The secondary structure of 16S ribosomal RNA contains forty-five double helices connected by short single-stranded segments. In the crystal structure, many of these helices are coaxially stacked with a helix neighboring in the sequence. There are 13 groups of coaxially stacked helices and 23 unstacked helices in 16S rRNA, for a total of 36 helical elements. There are three different types of helix-helix packing. Most of the helical elements are packed in a minor groove to minor groove fashion, which often requires distortions from canonical A-form helical geometry in one of the two helices. Adenosines from internal loops or from hairpin loops often mediate docking against an A-form double helix, with a dense network of base-2' OH and 2' OH-2' OH hydrogen bonds stabilising the packing. Less often, helix-helix packing occurs in a different mode, by insertion of a ridge of phosphates into a complementary minor groove of another helix. This packing mode is stabilized by hydrogen bonds between the ridge of phosphate oxygens and a layer of 2' OH and guanine base $NH_2$ groups. These guanine N2 groups are often made more accessible by the geometry of G-U pairs, which places this moiety farther into the minor groove than do Watson-Crick pairs. Finally, the rare end-on mode of interhelical packing uses a purine base to mediate the perpendicular packing of one helix against the minor groove of another helix. All three modes of helix-helix packing are further stabilized by idiosyncratic interactions between double-helical RNA and short non-helical RNA segments. Small bulges of one to three nucleotides are often found to pack either between helices or in the major groove of a helix.

The 5' Domain (fpd).

The fpd of 16S RNA contains 19 double helices, arranged as 7 groups of coaxially stacked helices and 5 unstacked helices, for a total of 12 double-helical elements packed tightly together. The result is a wedge-shaped mass of RNA that tapers to a single layer of double helices near the top of the domain. Like the other domains, the fpd is rather longer along the subunit interface than in the perpendicular direction.

The fpd can be divided into three subdomains, roughly corresponding to the upper, lower, and middle thirds of the secondary structure of the fpd. These subdomains make up the top and left-hand, the middle, and the lower right-hand sides of the body, respectively, in the view from 50S. The upper subdomain is a nearly planar arrangement of four helical elements (H16/H17, H4/H15, H1/H3, and H18). The H16/H17 stack forms the left-hand border of the body as viewed from 50S. This stack is almost 120 Å long, with H16 making contact with the head and H17 reaching the bottom of the subunit. Internal loops in both helices contain S-turns, which are used to modulate the position of the phosphate backbone in the case of H17, or to create an extended minor groove surface for helix-helix docking in the case of H16. The H4/H15 stack points towards the bottom of the subunit, with H15 well-packed against H17. The H1/H3 stack is bent by the conserved bulge at position 31, which results in the proximal end being horizontal and the terminal end pointing up to the head. The fourth helical element is H18, which is sharply bent to accommodate the 530 pseudoknot, defined by the unstacked helices 505–507/524–526 (H18.2) and 521–522/527–528 (H18.1). H18 is well-packed between the other two upwards-pointing elements of the upper subdomain, H1/H3 and H16. The 530 pseudoknot packs against the central pseudoknot at the H18.1-H1 interface.

The middle subdomain contains four helical elements (H5, H6, H12/H6A, and H13/H14) that form a layer between the upper and lower subdomains in the centre of the body. There are relatively few packing interactions within the subdomain, and several of its helices pack against the upper subdomain on one side and the lower subdomain on the other. Thus at the bottom of the subunit, the conserved root of H6 packs against H8 (lower subdomain) on one side and H15 (upper subdomain) on the other side. Similarly, the H12/H6A stack packs against H4 (upper subdomain) and H7 (lower subdomain). H12/H6A also packs against H5 and the 117 loop, which pack against elements from the upper and lower subdomains, respectively. H5 is well-packed against H15 and the 117 loop stacks with the root of H11. H5 also packs against the H13/H14 stack in the phosphate ridge-minor groove manner. H13/H14 interacts with two different regions of the lower subdomain. The conserved UACG hairpin loop at the end of H14 packs against the 160 GAAA hairpin from H8 while the large conserved hairpin at the end of H13 interacts with H7. This hairpin loop also makes many interactions with elements from the middle subdomain.

The lower subdomain is a collection of three helical elements that form an open saddle-shaped structure in the lower right-hand corner of the body. The H8/H9 stack stretches from the back of the subunit to the front, with the conserved 160 GAAA hairpin pointing toward the 50S subunit. It packs tightly against the H7/H10 stack at the 4-way junction that joins them, and again at a Thermus-specific interaction between insertions at nucleotides 190 and 129. The H7/H10 stack also makes weak interactions with H15 and H17 from the upper subdomain at the bottom of the subunit. H11 contains two sharp bends that allow its conserved terminal hairpin loop to pack against H7. Both bends are stabilized by short-range minor-groove to minor-groove packing contacts.

The Central Domain (cd).

The cd is the RNA component of the platform. Its fold based on our previous 5.5 Å structure [9] is in excellent agreement with our current structure. It contains nine helical elements folded into a W-shape in the 50S view. Two long single-stranded segments of RNA, the 570 and 820 loops, are also important structural elements. The domain is dominated by the long stack of H21/H22/H23, which forms the U-shaped perimeter of the domain. H21 is the only component of the left-hand arm of the W, while H22 and H23 form the base of the right-hand side. The right-hand arm of the W consists of H23B and H24A whose conserved hairpin loops are tightly packed. This arrangement requires sharp bends between H23 and H23B, and between H24 and H24A. The H23/H23B bend is stabilized by short-range minor groove-minor groove packing interactions. The H24/H24A bend is more unusual in that the bend is towards the major groove, which places a ridge of H24A phosphates in the major groove of H24. This major-groove bend is stabilized partly by short-range base-base and base-backbone interactions in the major groove of the bend, and partly by long-range interactions between the bent H24/H24A minor groove and the minor groove of H23. The heart of the central domain is the thicker middle arm of the W, which contains six helical elements (H20, H19/H25, H24, H26/H26A, H27, and H23B) and the 570 and 820 loops. On the left-hand side of the arm, the H26/H26A stack packs tightly against H22, the base of H25, and the 570 loop. The H25/H19 stack packs well with H20 and with the 570 loop. On the right-hand side of the central arm of the W, H23A packs well with H22, the 820 loop stacks on H24, and H24 packs well with the conserved GCAA hairpin loop of H27. In the centre of the arm, H23A packs with H26 in the phosphate ridge-minor groove manner, and the conserved H23A GAAG hairpin loop packs against H20. The 820 loop also interacts with H20, H25, and the 570 loop.

The 3' Major Domain (tmd).

The 3' major domain (tpd) is the RNA component of the head of the 30S subunit. From the 50S view, the left-hand side of the head tapers to a beak made of RNA on the 50S side and protein on the solvent side. Like the other domains, the tpd is relatively thin in the direction perpendicular to the intersubunit interface. The tpd consists of fifteen helical elements, most of which do not stack on a neighboring helix, in contrast to the extensive stacking of neigboring helices seen in the fpd and the central domain. The tpd can be divided into three subdomains, which correspond to the upper, middle, and lower portions of the tpd secondary structure. The upper subdomain is an extended structure in the part of the head farthest from the 50S subunit, and makes relatively few packing contacts with RNA from the other head subdomains. The lower and middle subdomains are more globular and are more intimately packed together, and make up the front-right and front-left portions of the head, respectively. The middle subdomain includes the RNA portion of the beak.

The upper subdomain contains three helical elements that make up a well-separated structure on the solvent side of the head. The subdomain is dominated by the H35-H36-H38-H39 stack, which stretches from the top to the bottom of the head. The other two helical elements of this subdomain are H37 and H40, which pack well with each other and loosely with the H35-H36-H38-H39 stack. The H37–H40 pack is mediated by a semiconserved GAAA hp in H40 with adjacent G-C pairs in H37.

The smaller middle subdomain is extended and contains only four helical elements, H32, H33/H33A, H33B and H34. Two of these (H33/H33A and H33B) form the Y-shaped RNA component of the beak. The H33/H33A stack points to the left in the 50S view while H33B points to the right, with its terminal conserved GNRA hairpin loop packed against H32, the covalent connection between the beak and the lower subdomain. H32 in turn packs against the H33-H34 junction as well as the 980 loop in the lower subdomain. With the exception of a small packing interaction with H32, the irregular H34 makes only long-range and somewhat tenuous packing interactions. The first is with H31 in the lower subdomain, an unusually weak minor-groove to minor groove packing. The second interaction is an unusual end-on packing interaction with the minor groove of the H34/H35/H38 junction in the upper subdomain.

The lower subdomain contains almost half of the tpd RNA and contains seven helical elements (H28/H29, H30, H31/980 loop, H41, H41A, H42 and H43) intimately packed into a globular mass Helices 42 and 43 are arranged in an approximately parallel fashion at the centre of the fold, and each interacts with at least three of the other helical elements. Helices 42 and 43 dock together by means of a minor-groove to minor-groove packing of their conserved hairpin loops. On the solvent side of the H42/H43 pair, H41 packs with both H42 and H43, while the terminal GCAA hairpin loop of H41A packs against H42. This arrangement requires a sharp bend between H41 and H41A, whose minor grooves pack against each other at the bend. The H43–H41 pack is made more extensive by an underwound A-rich internal loop in H41. On the 50S side of the central H42/H43 pair are H29, H30, H31 and the 980 loop. H43 is well-packed with H29 and makes weaker interactions with H30 and the 980 loop, while H42 is well-packed with H30 and the 980 loop. The H42–H30 pack is mediated by successive conserved G-A pairs at the base of H42. The H43–H29 pack is mediated by a conserved S-turn at the base of H43. An S-turn also mediates the packing of H42 with H41. H31 is a peripheral element of the subdomain, packing well only with H30, but also packs with H34 from the middle subdomain.

The 3' Minor Domain.

The 3' minor domain consists of just two helices at the subunit interface. H44 is the longest single helix in the subunit, and stretches from the bottom of the head to the bottom of the body. It projects prominently from the body for interaction with the 50S subunit. H45 is approximately perpendicular to H44, with its conserved GGAA hairpin loop packed against H44 and available for interaction with the large subunit.

Proteins in the 30S and Their Interaction with 16S RRNA

The current structure includes all of the 30S proteins except S1. The proteins generally consist of one or more folded domains, about half of which were known from previous work on isolated proteins. However, nearly all of the proteins contain extended termini or loops which interact intimately with RNA and were disordered in the isolated structures. Although most of the proteins form intimate contacts with ribosomal RNA, there are also protein-protein interactions such as those seen in the S4-S5-S8 and S3-S10-S14 clusters.

Proteins in the Central Domain (S18, S11, S8, S15).

S18: S18 in the 30S consists of residues 19–88. It consists of two helices, and a third helical element formed by two short turns from different parts of the structure that stack end-to-end. These helices together form a hydrophobic core. The C-terminus interacts with S11.

S11: S11 is a new structure and consists of two helices packed against a sheet, a type of fold seen in many ribosomal proteins. The sheet packs against the minor groove of the 690 loop (H23), and has a C-terminal extension that interacts with the C-terminal extension of S18 and also with the 790 loop (H24). Thus S11 stabilizes folding of the platform, by binding to both H23 and H24 near the tip of the platform.

S8: S8 binds near the H20/H21/H22 three-way junction and makes extensive interactions with H21 and H25. We now have molecular details of these interactions. In particular, two loops from S8 (87–92 and 112–118) wrap around the bulged bases 641–642 which were known to be required for high affinity binding of S8 [20, 21]. The N-terminus of the protein also packs against the minor groove of the 825 stem (H25), thus helping the folding of the central domain. Residues K55 on S8 and 653 on RNA are next to each other as would be expected from crosslinking [22]. The extension in Thermus S8 of the loop 69–76 packs against S2 from a symmetry related molecule.

S15: S15 binds between H20 and H22 near the three-way junction.

The 5' Domain Binding Proteins S17, S16 and S20.

S17: Although originally thought to be exclusively a 5' domain binding protein, S17 also binds near the H20/H21/H22 three-way junction. The core of S17 is known from NMR to be a β-barrel with an OB fold, with long extended loops [23]. These loops are disordered in solution but bind RNA in the 30S. In Thermus, there is a long C-terminal extension to S17 that is organized as an RNA-binding helix. The core of the protein and the C-terminal helix make extensive contacts with H11 and also contact H7. The C-terminal helix also contacts H21 in the central domain. Two long loops, loop 1 (26–36) and loop 2 (60–71) are ordered and interact with disparate domains of RNA exactly as predicted. Loop 1, which contains the site of neamine resistance, is inserted between H21 and a highly irregular structure at the base of H11. The very tip of loop 1 also touches the 560 loop of 16S RNA. Loop 2, which contains the site of a mutant defective in assembly, is involved in stitching together H7 and H11. Thus S17 interacts with H7, H11 and the 560 loop in the 5' domain, and H21 in the central domain.

S16: For a small protein, S16 has an extensive footprint throughout the 5' domain. All of the residues (1–88) are visible in the electron density, and were rebuilt using an NMR structure [24] as a guide. The protein consists of an N-terminal sheet with two extended loops, and two short helices in the C-terminal end. All of the extensive contacts with 16S RNA are now clear. The β-sheet is packed between the 608/620 internal loop of H21 on one side and a minor groove of H4 on the other. The two loops that extend out from this sheet both interact with RNA. Loop 1 interacts with phosphates in major groove of H4, while residues 39–43 in loop 2 make contact with the phosphate backbone around the internal loop near 453 in H17. The first helix (53–61) also extends across the major groove of this internal loop, while the C-terminal end of the second helix along with the turn leading out of it point into a minor groove of H17. There is also interaction with the 110 loop of the 5' domain. Finally, the extended C-terminus lies across the minor groove at the tip of H17.

S20: The current high resolution structure of S20 shows that the long N-terminal helix contacts the base of H6 and the tip of helix 44, and many conserved basic residues make salt-bridges with phosphates. Helices 2 and 3 of S20 interact with the minor groove of H9, and helix 3 also interacts with tip of H11 (263). Finally the extreme C-terminus of the protein is extended and lies along the minor groove of H9, which is longer in Thermus by 11 nucleotides. Thus S20 brings together several helices near the bottom of the subunit.

Proteins Near the Functional Centre.

S4, S5 and S12 are clustered near the "functional center" of the ribosome and contain the sites of several important mutations.

S4: In the structure of isolated S4 [25, 26] the N-terminal domain was cleaved off prior to crystallization. This N-terminal region is organized as a tightly folded domain with a metal ion (presumably zinc) that is coordinated by four cysteines. The domain is packed against the body of the protein. While the N-terminus of S4 is highly conserved, the cysteines themselves are not. It is therefore likely that the addition of a "zinc finger" is for additional stability rather than essential for the fold. The linker residues 46–52 connect the N-terminal domain with the rest of the protein. All domains of S4 make intimate contacts with RNA. In particular, S4 makes extensive contacts with a five-way junction where H3, H4, H16, H17 and H18 come together in the 5' domain.

The N-terminal domain is packed against the 420 stem-loop (H16). The largely helical domain I is packed against a complicated region of RNA where H3 and the 507 bulge at the base of H18 come together. The remaining domain of S4 makes extensive contact with the minor groove of the base of H16. In addition, it also makes contact with the tip of the H21, which is itself packed against H4.

This position is consistent with the large body of biochemical data on S4 binding to 16S RNA.

The C-terminus of S4 makes an extensive interface with S5. Most of the known mutations of S4 and S5 that confer the ram phenotype are located in this region [27, 28]. The interface consists of several highly conserved salt bridges, and some of the mutations break one or more of these interactions.

S5: The structure of S5 shows that the loop from residues 14–28 is folded back onto the body of the protein in the isolated structure, but is a filly extended β-hairpin in the 30S. Also, the C-terminus of S5, which is disordered in the isolated structure, is mainly helical and packs against a complicated surface of S8 formed by many different strands.

S5 interacts closely with a region of the ribosome where the head and the body come together. In the head, the extended H35/H36 helix packs against H28, which forms the neck of the 30S connecting the body with the head. The tip of H36 makes contact with H26a, H2 and the central pseudoknot in the body. Protein S5 has contacts throughout this region, thereby stabilizing the conformation of the head with respect to the body.

The C-terminal sheet of S5 makes extensive interactions with the major groove of the H1 and the central pseudoknot. The N-terminal domain binds to the major groove of H36, as does the base of the β-hairpin. The tip of the hairpin interacts with the phosphate backbone in H28 and is also very close to H34. Nucleotide 560 is very close to K121 in agreement with crosslinking data.

Most of the extensive interactions with RNA occur via major grooves or phosphate backbone.

S12: S12 is unusual both for its structure and location. It is unique among the 30S proteins in being on the interface side of the subunit. Its central core consists of a b-barrel with an OB fold, a feature found in other proteins such as S17. This core binds together H18, the 530 stem loop (at the tip of H18), H3 and a part of H44 close to the decoding site. An unusual feature is a long extension that connects this core with a short helix at the N-terminus of the protein. This extension threads between the 560 loop and H12 on one side, and H11 on the other, to make contact with both S8 and S17 on the other side of the 30S.

S12 is also the only protein in the vicinity of the decoding site near 1492–1493 of RNA. It is the site of a number of functionally interesting mutations.

The Head Proteins S7 and S9.

S7: Protein S7, whose structure in isolation was previously known, is known to be crucial for the assembly of the head [29]. In our 30S structure, the entire sequence is visible, including the very basic N-terminus. S7 binds to a small but complex region of the tpd that encompasses two multiple-stem junctions at a comer of the head. The majority of the interaction surface consists of H29 tightly docked to the S-turn at the base of H43. This docking requires a tight turn at 1346, probably stabilized by S7 binding. Because S7 also makes interactions with H28, its primary surface of interaction encompasses all three of the helices around the H28/H29/H43 three-way junction. The very tight docking of H29 to H43 gives rise to a small region of very high negative charge density, which is bound by a surface of S7 with very high concentration of positive charge (mainly S7 helices 1 and 4).

The second important interaction surface is centred on the second multiple stem junction that S7 binds, the H29/H30/H41/H42 junction. In this junction, H30 and the base of H42 are tightly packed together, with a tight turn between them. An S-turn between helices 41 and 42 mediates packing of H41 and H42, which also have a tight turn between them. H41 also packs very tightly against H43. S7 makes contacts to the phosphate backbone of H41, stabilizing its packing with H43, and to residues around 1240 and 1298 where the tight bends occur in the H29/H30/H41/H42 junction. Contacts with U1240 are particularly intimate: the universally conserved bulge U1240 is deeply buried into a conserved hydrophobic pocket between the 35 and 115 loops of S7.

The β-hairpin is not tightly associated with 16S RNA, but probably fits tightly into the minor groove of the E-site tRNA. The structure is in rough agreement with a model of S7 binding to ribosomal RNA [30], but there are also significant differences, including the location of H43.

S9: S9 consists of a compact RNA-binding domain consisting of 2 helices packed against a 5-stranded sheet, with a third short helix at the C-terminal end of the domain. From this domain, there is a long 25 residue C-terminal tail that snakes into elements of the head RNA. S9 also interacts with S7 via a small hydrophobic patch.

The sheet of S9 makes extensive interactions with H38 and H39. It also has two loops that interact with the 1250 internal loop of H41. The short C-terminal helix interacts with 1177–1180 in H40.

The long C-terminal extension snakes between the H29–H43 junction on one side and the H38–H34 junction on the other to touch a portion of H31.

The S3 S10 S14 Cluster.

These three proteins form a cluster on the rear left-hand of the head, as the protein portion of the beak. S3 is clearly stacked on top of the other two proteins, consistent with the order of assembly.

S14: S14 is bound in a crevice in the RNA and is mostly covered by S3 and S10. Almost the whole molecule contacts RNA, including helices H31, H32, H34, H38, and H43. A cross linked residue is in close proximity to the RNA 28.

S14 contains a zinc ion coordinated by four cysteines from a CXXC-X12-CXXC (SEQ ID NO: 1) motif. This motif is structurally similar to that found in the first zinc finger in the glucocorticoid receptor. This zinc binding motif is not conserved among all bacteria, although many of the residues surrounding it are, suggesting perhaps that in other organisms the protein folds via a hydrophobic core.

S10: S10 is structurally very similar to the S6 fold, with two helices packed against a 4-stranded sheet. Two of the strands in this sheet are connected by a long β-hairpin that extends out from the sheet and is inserted right into the centre of the head RNA fold. The β-hairpin makes most of the contacts with RNA, including helices H31, H34 and H41. The two strands of the sheet pack into the shallow minor groove of H39, making contacts with backbone residues on both sides of the groove.

S3: S3 contains two domains, both consisting of two helices packed against a 4-stranded sheet, which is similar to several other ribosomal proteins. In addition to the domains there is an N-terminal tail (all of which is visible). The C-terminal 30 residues are poorly conserved and disordered in the structure.

RNA contact is made by the N-terminal tail and the C-terminal domain. The N-terminal tail fits into a major groove of H34. The sheet in the C-terminal domain also packs against H34.

The N-terminal domain makes few if any contacts with the RNA, but is mainly involved with making protein contacts with S10 and S14.

S13 and S19.

S13 and S19 form a loose dimer at the very "top" of the interface side of the head, extending both above and closer to the 50S than any of the head RNA. In spite of their location in this flexible region, they are both relatively well-defined in the electron density. Except for the C-terminal tail of S13, which reaches into the head and almost touches the tail of S9, none of these proteins are in contact with any other of the proteins in the small subunit. Together with S12, S11 and S15, these are among the few proteins that surround the region of intersubunit contact.

S13: All 125 residues of S13 are visible in the structure. The N-terminus (about 60 residues) forms a compact domain consisting of three small helices. Of this domain, only a small loop is in contact with the RNA and the domain appears to be clinging to the subunit only by virtue of its highly extended C-terminal region. This region begins with a long, straight alpha-helix that creeps along the top of the 30S head towards S19. It interacts mainly with the 1300 loop and H42. At this point the polypeptide chain bends by about 90 degrees, and the rest of the protein is mostly lacking in any secondary structure. This extended region curves around H41 into the head where it is buried in the RNA about 50–60 Å from the globular, N-terminal domain. It contacts H30 in the head.

S19: S19 consists of 92 residues. An NMR structure of isolated S19 [31] showed a single globular domain consisting of a helix packed against a three-stranded sheet, in which residues 9–78 were ordered. In the 30S structure, residues 2–81 are visible in the electron density. The C-terminus of the protein points towards the interface side and may become ordered in the 70S complex. Like S13, most of the globular domain of S19 is well separated from the RNA, but here both the N- and C-terminal extensions to the globular domain, as well as the loops 68–73 and 34–39 make contacts with H42. The C-terminal extension, like S13, bends around the RNA, to contact H31 while the N-terminus reaches H42 some considerable distance away. Thus, S19 straddles a portion of the head of the 30S. The residues in S13 and S19 that were crosslinked 48 are adjacent to each other in the structure.

S2.

Thermus S2 consists of 256 residues of which 7–235 are visible in our structure. The protein consists of a large central domain of about 200 residues that consists of a 5-stranded parallel sheet and four helices connecting them. Two helices that form a small coiled-coil motif protrude out of this domain. The protein is located on the back of the 30S at the interface between the head and the rest of the particle. While it is primarily regarded as a "head" protein, it also makes contacts with the central domain in our structure.

Thx.

This small 26 residue peptide was isolated and characterized from Thermus ribosomes [18]. Thx fills a cavity formed by a number of different elements at the very top of the head. Residues 1–24 are visible in the electron density, of which 8–14 form a short helix, flanked by extended ends. It is surrounded by H42, the tip of H41, and the base of H41, while the bottom of the cavity is formed by the major groove of H43. The protein is highly basic, and there are extensive salt-bridges between these residues and phosphates of nearby RNA. Thus Thx stabilizes a number of different RNA elements that come close together near the top of the head.

Functional Insight from the Structure of the 30S Ribosomal Subunit

During translation of the genetic code, the 30S ribosomal subunit provides the framework for base-paring between the anticodon of tRNA and the codon of mRNA, and discriminates between cognate and non-cognate tRNAs to ensure translational fidelity, in a process termed decoding. During translocation, the ribosome must move by precisely one codon relative to mRNA and the bound tRNAs. Both decoding and translocation involve "switches" in which precise conformational changes occur in the ribosome. The atomic resolution structure of the 30S subunit allows us to interpret the environment of the mRNA and tRNA binding sites in molecular terms. In one well-characterized example of a functional switch involved in accuracy, we are also able to determine the spatial arrangement of its elements, thus elucidating its architecture. The structure also suggests other possible switching elements in the 30S, and sheds light on the kinds of movements that might occur.

The ribosome contains three tRNA binding sites, designated A (aminoacyl), P (peptidyl) and E (exit), after their respective tRNA substrates. Each site is bipartite, located partly on the 30S ribosomal subunit and partly on the 50S subunit. The A- and P-site tRNAs bind with their aminoacyl acceptor ends on the 50S subunit, and with their anticodon ends base-paired to adjacent mRNA codons on the 30S subunit. The E-site tRNA is bound in a similar orientation but it is not known whether the E-site tRNA is base-paired to the E-site mRNA codon. The 30S subunit also binds mRNA upstream and downstream of the A, P and E codons. During translation, incoming aminoacyl tRNA is delivered to the A-site as a ternary complex with EF-Tu and GTP. Discrimination of cognate from non-cognate tRNAs occurs in the A-site. It is thought that there is also a second "proofreading" discrimination step in the A-site after GTP hydrolysis by EF-Tu, which is needed to discriminate cognate from near-cognate tRNAs. The 30S P-site has a much higher affinity for tRNA, in order to maintain the reading frame.

There is one well-characterized conformational switch in the 30S subunit, the helix 27 accuracy switch [32]. Genetic and biochemical data support a model in which this switch may be part of a larger-scale conformational change that occurs between initial selection and proofreading of the A-site tRNA, or the switch may play a role in translocation.

Until recently, there has been a large disparity between the high resolution of the genetic and biochemical data that define the RNA components of the active sites of the 30S subunit, and the relatively low-resolution of the three-dimensional structures of ribosomes available. The present invention addresses this disparity. In combination with previous biochemical and other data, it is now possible to identify the detailed structure of 30S active sites. In addition, by superimposing the tRNA and mRNA coordinates from the known 7.8 Å 70S structure, it is now possible to infer many of the interactions between 30S active sites and tRNA/mRNA ligands.

With our complete and high resolution structure of the 30S subunit in hand, it is now possible to identify at the residue level the elements of the 30S subunit that interact with the anticodon stem-loop (ASL) of the A, P and E-site tRNAs and associated mRNA.

Identification of the precise boundaries of the A, P, and E sites in an unbiased fashion in a structure determined in the absence of cognate tRNA ligands would normally be problematic. As it happens, the P-site in the 30S structure is filled with a stem-loop of RNA corresponding to residues 75–95 (in the E. coli numbering system) from the end of the "spur" (H6) of a neighbouring molecule. (Henceforth the term "spur" will refer to the symmetry-related spur docked in the P-site, rather than the spur at the bottom of the same subunit). The spur appears to mimic P-site tRNA by a variety of criteria. The extent of the 30S interaction with the anticodon stem-loop (ASL) is in very good agreement with that determined by affinity measurements [33] and by hydroxyl radical footprinting [34]. Secondly, the conformation of the spur stem-loop is distorted in order to more closely resemble the canonical tRNA ASL conformation [35, 36]: a U-A base pair is broken so that the spur hairpin loop can approximate the conformation of a tRNA ASL, complete with a U-turn and stacked anticodon. Another indication that the spur is a mimic of a bound P-site tRNA ASL is that of the twelve hydrogen bonds between 30S and the spur, only one appears to be sequence-specific, in accordance with the lack of sequence conservation in tRNA anticodon stems. Finally, close contacts of the spur with 16S RNA are on the whole consistent with chemical protection data for P-site tRNA [37] and with the 34-C1400 UV-induced crosslink between tRNA and 16S RNA [38] (the analogous residues are stacked in the 30S crystal structure).

Yet another indication that the spur mimics a P-site tRNA ASL is that its "pseudo-anticodon" is base-paired to a triplet of nucleotides, a mimic of mRNA. A fourth nucleotide is also visible 5' to the pseudo-anticodon, in the E site. These pseudo-codon bases are clearly pyrimidines, and appear to be UCU from the base-pairing geometries, which are U-U, U-C, and U-U since the pseudo-anticodon is UUU. The origin of this "pseudo-message" is unclear, but it probably comes from the 3' end of 16S RNA, which ends with 5' U1542C 1543U1544 3'. The last nucleotide of our 16S model is C1533, so that seven disordered nucleotides would span the 25 Å gap between C1533 and U1541, which is clearly stereochemically feasible. Alternatively, it is possible that the 3' end of 16S RNA has been cleaved somewhere between C1533 and U1541 prior to or during crystallization. The presence of functional mimics of mRNA and P-site tRNA also explains why these crystals diffract relatively well: the P-site tRNA makes extensive contacts with both the head and the body of the 30S, thereby helping to lock the particle into a single conformation.

To ask how well pseudomessage and spur mimic mRNA and the ASL of tRNA, we have used the 7.8 Å resolution structure of the 70S ribosome with bound mRNA and tRNAs [39]. In that structure, two elements of 16S RNA were identified, H27 and H44. To avoid any possible bias in our interpretation of the spur as a mimic, only H27 and H44 were used to in the alignment to superimpose the 70S structures onto our 30S structure. Despite the relatively low resolution of the 70S structure used, a least-squares superposition of these two elements had a phosphate r.m.s.d. of only 2.3 Å. When the 70S elements are superimposed in this manner onto our 30S structure, we found that indeed, as expected, the P-site tRNA superimposes well onto the 30S spur, and the 30S pseudo-message corresponds to the P-site codon. In particular, the orientation of the spur stem-loop is very similar to the 70S P-site ASL, and there are no significant clashes between the 70S A- and E-site tRNAs and our 30S subunit when superimposed in this manner. It is clear that the spur and pseudo-message cannot be perfect mimics, however, because the pseudo-anticodon—codon helix consists of three pyrimidine-pyrimidine base pairs, which are about 2 Å narrower than Watson-Crick pairs. Thus it seems likely that the spur and its pseudo-message are good but not perfect mimics of P-site tRNA and P-site codon, respectively, and that the spur mimic model should explain many but perhaps not all features of P-site tRNA binding to the 30S. Moreover, the transformed A- and P-site tRNAs and A-site codon provides a useful landmarks for modeling the extent of the A- and E-sites of the 30S.

The P-site.

The P-site spur contacts several discrete regions of 16S RNA, most of which have been implicated in P-site binding by biochemical experiments. Two proteins also participate in binding the P-site ASL, a possibly surprising result. Most of the contact surface lies between the minor groove of the spur stem and 16S RNA nucleotides 1338–1341, 1229–1230, and the C-terminal tails of proteins S13 and S9. There are many hydrogen bonds between the minor groove (i.e. the 2' OH and base groups) of spur residues C91, C92, and G78 and the minor groove surface of G1338-A1339. Only one of these hydrogen bonds appears to be sequence-specific (G78 N2-A1339 N3). A contact from Lys 126 of S9 appears to help stabilize this minor-groove to minor-groove packing interaction. Both 1338 and 1339 have previously been implicated in P-site binding [37]. A second area of contact, nearly continuous with the first, is between the 16S 1229–1230 sugar-phosphate backbone and spur residues G77 and G78. This region of contact is extended by the C-terminal tail of S13, which seems to help glue the spur and the 1229–1230 area together. The other areas of contact are much more tenuous. One interaction is stacking of U82 on C1400, which rationalizes the ASL 34-C1400 uv-induced crosslink [38]. The other is a packing interaction between A790 and spur residues 88–89, with a single hydrogen bond present. A790 is a so-called class III site, that is it is protected by either tRNA or 50S subunits. From the spur interaction, it would thus appear that binding of either the 50S subunit or the P-site ASL stabilizes a contact between A790 N6 and the phosphate of 1498, i.e. a contact between the central and three-prime minor domains. Finally, if the pseudo-codon—pseudo-anticodon helix were a few Å wider, as it would be for a Watson-Crick-paired helix, it would make van der Waals contact with the base of G966. G966 has also previously been implicated as part of the P-site by chemical modification experiments and has also been identified as a one of the few guanines crucial for P-site binding [40].

The P-site codon is threaded through the major groove of the upper portion of helix 44, in a universally conserved region of 16S RNA. There appears to be a tight turn between nucleotides −1 and +1, that is, between the last E-site and the first P-site codon nucleotides. This tight turn is stabilized by a hydrogen bond to the N1/N2 groups of the conserved residue G926, a residue previously implicated as crucial for P-site binding [40]. Additional hydrogen bonds are seen between the 2' OH of +1 to the phosphate of C1498, and between the phosphate of +2 and the 2' OH of C1498. The phosphate of +2 also stacks on the base of C1498. The phosphate of +3 is within hydrogen-bonding distance of two conserved cytidine N4 groups, from C1402 and C1403. The +3 base also stacks on the sugar of C1400. Finally, it appears likely that there are several magnesium ions that may help stabilize the location of the P-site codon in the major groove of H44.

The E-site.

The E-site is defined by the environment surrounding the 70S E-site tRNA superimposed onto our 30S structure, as described above. Unlike the A and P-sites, the E-site consists mostly of protein. Proteins S7 and S11 have a small interface that binds the minor groove of the E-site ASL. The highly conserved beta-hairpin of S7 extends this surface nearly to the bottom of the anticodon, and it is possible that the S7 beta-hairpin helps dissociate the E-site codon from the E-site anticodon. The RNA portion of the E-site makes only tenuous interactions with the E-site ASL. 16S nucleotides 1382 and 1383 may interact with residue 34 of the anticodon. The minor-groove surface of the conserved 16S residues 693 and 694 may interact with the minor-groove surface of the 37–39 residues of the E-site ASL.

The A-site.

The A-site is rather wider and shallower than the P or E sites, perhaps in order to allow rotation of the A-site codon-anticodon helix during or after GTP hydrolysis by EF-Tu. The RNA components of the A-site appear to include portions of the 530 loop, H34 in the head, and residues 1492–1493 from the 3' minor domain, all of which have been previously implicated in A-site binding.

The Helix 27 Switch.

It is clear that many of the elements that make contact with the various tRNA would have to move during translocation. Indeed, the ribosome is known to undergo extensive conformational changes during the elongation cycle, and these must involve breaking and making precise contacts.

However, the precise switching elements in these conformational changes are not known in general, with the exception of a switch in H27.

H27 is proposed to have two alternative base-pairing schemes during translation, one a "ram" or permissive form that pairs 885–887 with 910–912, and an alternative "restrictive" form that pairs 888–890 with 910–912 [32]. The ram form appears to be the more stable form in the ribosome and it features an S-turn (or loop E motif) in H27. The S-turn in H27 is also seen in the tRNA-bound structure of the 70S [39]. A switch to the restrictive form would involve a sliding of the two strands of H27 relative to each other and the S-turn would be replaced by an internal loop with a different structure for H27. Indeed, analysis of the two forms by cryoelectron microscopy reveal noticeable conformational changes in the ribosome, especially around the A-site [41]. We can now precisely define the structure around H27 and use previous chemical modification data [32] to suggest the kinds of movement involved.

The S-turn in H27 around 888 is right next to 1489 in H44, and H27 packs against the minor groove of H44 just below the decoding site. The tip of H27 is close to H11, while 885, which is base-paired with 910 in our conformation, is near both H1 and the 570 loop. Finally, 914 is near both H1 and 526 in the 530 loop. Thus H27 is right in the heart of an area which includes the decoding site and the 530 loop. So it is not surprising that a change in the conformation of H27 would have affect these elements.

A number of elements that are more accessible in the "restrictive" state appear to be protected in the structure of the present invention. Thus for example, 524–526 are currently base-paired with 507–505 in the 530 pseudoknot. This suggests that the 530 pseudoknot could be broken in the restrictive state. Similarly, 1053 and 1197 are base-paired in the current structure, but they are part of a distorted region of H34 analogous to an S-turn, and it is not hard to envisage that an analogous switch might occur in H34 in the alternative state. Thus the data in combination with our structure suggests that H34 in the head and the 530 loop in the shoulder move between the two states, with H34 possibly adopting an alternative form, and the 530 pseudoknot being disrupted. In this context, it is interesting to note that both H34 and the 530 loop have been implicated in tRNA binding.

Other parts of the chemical protection data, especially those that are supposed to indicate enhanced accessibility in the ram state, are not so easy to rationalize since they involve protected bases in our structure.

The 30S structure has allowed us to identify details of the tRNA and mRNA binding sites, as well as obtain our first detailed look at the structure around the H27 switch. Clearly, H27 is only one component of major conformational changes that occur during translation. Analysis of the high resolution 30S structure should allow us to identify other potential switching elements, which may then be tested genetically.

Although the foregoing invention has been described in some detail by way of illustration and example for purposes of clarity of understanding, it will be apparent to those skilled in the art that certain changes and modifications may be practiced. Therefore, the descriptions and examples should not be construed as limiting the scope of the invention, which is delineated by the appended claims.

References:
1. Garrett, R. A. et al. (eds.) The Ribosome. Structure, Function, Antibiotics and Cellular Interactions (ASM Press, Washington, D.C., 2000).
2. von Böhlen, K. et al. Characterization and preliminary attempts for derivatization of crystals of large ribosomal subunits from Haloarcula marismortui diffracting to 3 Å resolution. J. Mol. Biol. 222, 11–15 (1991).
3. Trakhanov, S. D. et al. Crystallization of 70 S ribosomes and 30 S ribosomal subunits from *Thermus thermophilus*. FEBS Lett. 220, 319–322 (1987).
4. Glotz, C. et al. Three-dimensional crystals of ribosomes and their subunits from eu- and archaebacteria. Biochem. Int. 15, 953–960 (1987).
5. Yonath, A. et al. Characterization of crystals of small ribosomal subunits. J. Mol. Biol. 203, 831–834 (1988).
6. Yusupov, M. M., Tischenko, S. V., Trakhanov, S. D., Ryazantsev, S. N. & Garber, M. B. A new crystalline form of 30 S ribosomal subunits from *Thermus thermophilus*. FEBS Lett. 238, 113–115 (1988).
7. Yonath, A. et al. Crystallographic studies on the ribosome, a large macromolecular assembly exhibiting severe nonisomorphism, extreme beam sensitivity and no internal symmetry. Acta Crystallogr A54, 945–55 (1998).
8. Tocilj, A. et al. The small ribosomal subunit from *Thermus thermophilus* at 4.5 A resolution: pattern fittings and the identification of a functional site. Proc Natl Acad Sci USA 96, 14252–7(1999).

9. Clemons, W. M., Jr. et al. Structure of a bacterial 30S ribosomal subunit at 5.5 Å resolution. Nature 400, 833–840 (1999).
10. Otwinowski, Z. & Minor, W. in Methods in Enzymology (eds. Carter, C. W. J. & Sweet, R. M.) 307–25 (Academic Press, New York, 1997).
11. Terwilliger, T. & Berendzen, J. Automated MAD and MIR structure determination. Acta Cryst D55, 849–861 (1999).
12. Abrahams, J. P. Bias reduction in phase refinement by modified interference functions: introducing the gamma correction. Acta Cryst. D53 (1997).
13. de la Fortelle, E. & Bricogne, G. in Methods in Enzymology (eds. Carter, C. W., Jr. & Sweet, R. M.) 472–93 (Academic Press, New York, 1997).
14. Hartmann, R. K. & Erdmann, V. A. Thermus thermophilus 16S rRNA is transcribed from an isolated transcription unit. J Bacteriol 171, 2933–41 (1989).
15. Cowtan, K. & Main, P. Miscellaneous algorithms for density modification. Acta Crystallogr D Biol Crystallogr 54, 487–93 (1998).
16. Jones, T. A. & Kjeldgaard, M. Electron-density map interpretation. Meth. Enzymol. 277B, 173–207 (1997).
17. Brünger, A. T. et al. Crystallography & NMR system: A new software suite for macromolecular structure determination. Acta Crystallogr D Biol Crystallogr 54, 905–21 (1998).
18. Choli, T., Franceschi, F., Yonath, A. & Wittmann-Liebold, B. Isolation and characterization of a new ribosomal protein from the thermophilic eubacteria, *Thermus thermnophilus, T. aquaticus* and *T. flavus*. Biol Chem Hoppe Seyler 374, 377–83 (1993).
19. Mueller, F. & Brimacombe, R. A new model for the three-dimensional folding of *Escherichia coli* 16 S ribosomal RNA. I. Fitting the RNA to a 3D electron microscopic map at 20 A. J Mol Biol 271, 524–44 (1997).
20. Mougel, M. et al. Minimal 16S rRNA binding site and role of conserved nucleotides in *Escherichia coli* ribosomal protein S8 recognition. Eur J Biochem 215, 787–92 (1993).
21. Wu, H., Jiang, L. & Zimmermann, R. A. The binding site for ribosomal protein S8 in 16S rRNA and spc mRNA from *Escherichia coli*: minimum structural requirements and the effects of single bulged bases on S8-RNA interaction. Nucleic Acids Res 22, 1687–95 (1994).
22. Urlaub, H., Thiede, B., Muller, E. C., Brimacombe, R. & Wittmann-Liebold, B. Identification and sequence analysis of contact sites between ribosomal proteins and rRNA in *Escherichia coli* 30 S subunits by a new approach using matrix-assisted laser desorption/ionization-mass spectrometry combined with N-terminal microsequencing. J Biol Chem 272, 14547–55 (1997).
23. Golden, B. L., Hoffman, D. W., Ramakrishnan, V. & White, S. W. Ribosomal protein S17: characterization of the three-dimensional structure by 1H- and 15N-NMR. Biochemistry 32, 12812–20 (1993).
24. Allard, P. et al. Another piece of the ribosome: Solution structure of S 16 and its location in the 30S subunit. Structure, (2000).
25. Davies, C., Gerstner, R. B., Draper, D. E., Ramakrishnan, V. & White, S. W. The crystal structure of ribosomal protein S4 reveals a two-domain molecule with an extensive RNA-binding surface: one domain shows structural homology to the ETS DNA-binding motif. Embo J 17, 4545–58 (1998).
26. Markus, M. A., Gerstner, R. B., Draper, D. E. & Torchia, D. A. The solution structure of ribosomal protein S4 delta41 reveals two subdomains and a positively charged surface that may interact with RNA. Embo J 17, 4559–71 (1998).
27. van Acken, U. Proteinchemical studies on ribosomal proteins S4 and S12 from ram (ribosomal ambiguity) mutants of *Escherichia coli*. Mol Gen Genet 140, 61–8 (1975).
28. Wittmann-Liebold, B. & Greuer, B. The primary structure of protein S5 from the small subunit of the *Escherichia coli* ribosome. FEBS Lett 95, 91–8 (1978).
29. Nowotny, V. & Nierhaus, K. H. Assembly of the 30S subunit from *Escherichia coli* ribosomes occurs via two assembly domains which are initiated by S4 and S7. Biochemistry 27, 7051–5 (1988).
30. Tanaka, I. et al. Matching the crystallographic structure of ribosomal protein S7 to a three-dimensional model of the 16S ribosomal RNA. Rna 4, 542–50 (1998)
31. Helgstrand, M. et al. Solution structure of the ribosomal protein S19 from *Thermus thermophilus*. J Mol Biol 292, 1071–81 (1999).
32. Lodmell, J. S. & Dahlberg, A. E. A conformational switch in *Escherichia coli* 16S ribosomal RNA during decoding of messenger RNA. Science 277, 1262–7 (1997).
33. Rose, S. J. d., Lowary, P. T. & Uhlenbeck, 0. C. Binding of yeast tRNAPhe anticodon arm to *Escherichia coli* 30 S ribosomes. J Mol Biol 167, 103–17 (1983).
34. Huttenhofer, A. & Noller, H. F. Hydroxyl radical cleavage of tRNA in the ribosomal P-site. Proc Natl Acad Sci USA 89, 7851–5 (1992).
35. Jack, A., Ladner, J. E. & Klug, A. Crystallographic refinement of yeast phenylalanine transfer RNA at 2–5A resolution. J Mol Biol 108, 619–49 (1976).
36. Rich, A. & RajBhandary, U. L. Transfer RNA: molecular structure, sequence, and properties. Annu Rev Biochem 45, 805–60 (1976).
37. Moazed, D. & Noller, H. F. Binding of tRNA to the ribosomal A and P-sites protects two distinct sets of nucleotides in 16 S rRNA. J Mol Biol 211, 135–45 (1990).
38. Prince, J. B., Taylor, B. H., Thurlow, D. L., Ofengand, J. & Zimmermann, R. A. Covalent crosslinking of tRNA1Val to 16S RNA at the ribosomal P-site: identification of crosslinked residues. Proc Natl Acad Sci USA 79, 5450–4 (1982).
39. Cate, J. H., Yusupov, M. M., Yusupova, G. Z., Earnest, T. N. & Noller, H. F. X-ray crystal structures of 70S ribosome functional complexes see comments]. Science 285, 2095–104 (1999).
40. von Ahsen, U. & Noller, H. F. Identification of bases in 16S rRNA essential for tRNA binding at the 30S ribosomal P-site. Science 267, 234–7 (1995).
41. Gabashvili, I. S. et al. Major rearrangements in the 70S ribosomal 3D structure caused by a conformational switch in 16S ribosomal RNA. Embo J 18, 6501–7 (1999).

TABLE 2

| | |
|---|---|
| | REMARK 465 GLU B 255 |
| | REMARK 465 ALA B 256 |
| REMARK 465 MISSING RESIDUES | REMARK 465 MET C 1 |
| REMARK 465 THE FOLLOWING | REMARK 465 ILE C 208 |
| RESIDUES WERE NOT LOCATED IN | REMARK 465 GLY C 209 |
| THE | REMARK 465 GLY C 210 |
| REMARK 465 EXPERIMENT. | REMARK 465 GLN C 211 |
| (M = MODEL NUMBER; RES = RESIDUE | REMARK 465 LYS C 212 |
| NAME; C = CHAIN | REMARK 465 PRO C 213 |
| REMARK 465 IDENTIFIER; | REMARK 465 LYS C 214 |
| SSSEQ = SEQUENCE NUMBER; | REMARK 465 ALA C 215 |

TABLE 2-continued

| | |
|---|---|
| I = INSERTION CODE.) | REMARK 465 ARG C 216 |
| REMARK 465 | REMARK 465 PRO C 217 |
| REMARK 465 M RES C SSSEQI | REMARK 465 GLU C 218 |
| REMARK 465 U A 0 | REMARK 465 LEU C 219 |
| REMARK 465 U A 1 | REMARK 465 PRO C 220 |
| REMARK 465 U A 2 | REMARK 465 LYS C 221 |
| REMARK 465 G A 3 | REMARK 465 ALA C 222 |
| REMARK 465 U A 4 | REMARK 465 GLU C 223 |
| REMARK 465 C A 1535 | REMARK 465 GLU C 224 |
| REMARK 465 C A 1536 | REMARK 465 ARG C 225 |
| REMARK 465 U A 1537 | REMARK 465 PRO C 226 |
| REMARK 465 C A 1538 | REMARK 465 ARG C 227 |
| REMARK 465 C A 1539 | REMARK 465 ARG C 228 |
| REMARK 465 U A 1540 | REMARK 465 ARG C 229 |
| REMARK 465 U A 1541 | REMARK 465 ARG C 230 |
| REMARK 465 U A 1542 | REMARK 465 PRO C 231 |
| REMARK 465 C A 1543 | REMARK 465 ALA C 232 |
| REMARK 465 U A 1544 | REMARK 465 VAL C 233 |
| REMARK 465 MET B 1 | REMARK 465 ARG C 234 |
| REMARK 465 PRO B 2 | REMARK 465 VAL C 235 |
| REMARK 465 VAL B 3 | REMARK 465 LYS C 236 |
| REMARK 465 GLU B 4 | REMARK 465 LYS C 237 |
| REMARK 465 ILE B 5 | REMARK 465 GLU C 238 |
| REMARK 465 THR B 6 | REMARK 465 GLU C 239 |
| REMARK 465 GLU B 241 | REMARK 465 MET D 1 |
| REMARK 465 ALA B 242 | REMARK 465 MET E 1 |
| REMARK 465 GLU B 243 | REMARK 465 PRO E 2 |
| REMARK 465 ALA B 244 | REMARK 465 GLU E 3 |
| REMARK 465 THR B 245 | REMARK 465 THR E 4 |
| REMARK 465 GLU B 246 | REMARK 465 GLU E 155 |
| REMARK 465 THR B 247 | REMARK 465 ALA E 156 |
| REMARK 465 PRO B 248 | REMARK 465 HIS E 157 |
| REMARK 465 GLU B 249 | REMARK 465 ALA E 158 |
| REMARK 465 GLY B 250 | REMARK 465 GLN E 159 |
| REMARK 465 GLU B 251 | REMARK 465 ALA E 160 |
| REMARK 465 SER B 252 | REMARK 465 GLN E 161 |
| REMARK 465 GLU B 253 | REMARK 465 GLY E 162 |
| REMARK 465 VAL B 254 | REMARK 465 MET G 1 |
| REMARK 465 MET I 1 | REMARK 465 ALA R 12 |
| REMARK 465 MET J 1 | REMARK 465 GLN R 13 |
| REMARK 465 PRO J 2 | REMARK 465 ARG R 14 |
| REMARK 465 VAL J 101 | REMARK 465 ARG R 15 |
| REMARK 465 GLY J 102 | REMARK 465 MET S 1 |
| REMARK 465 GLY J 103 | REMARK 465 GLY S 82 |
| REMARK 465 GLY J 104 | REMARK 465 HIS S 83 |
| REMARK 465 ARG J 105 | REMARK 465 GLY S 84 |
| REMARK 465 MET K 1 | REMARK 465 LYS S 85 |
| REMARK 465 ALA K 2 | REMARK 465 GLU S 86 |

TABLE 2-continued

| | |
|---|---|
| REMARK 465 LYS K 3 | REMARK 465 ALA S 87 |
| REMARK 465 LYS K 4 | REMARK 465 LYS S 88 |
| REMARK 465 PRO K 5 | REMARK 465 ALA S 89 |
| REMARK 465 SER K 6 | REMARK 465 THR S 90 |
| REMARK 465 LYS K 7 | REMARK 465 LYS S 91 |
| REMARK 465 LYS K 8 | REMARK 465 LYS S 92 |
| REMARK 465 LYS K 9 | REMARK 465 LYS S 93 |
| REMARK 465 VAL K 10 | REMARK 465 MET T 1 |
| REMARK 465 MET L 1 | REMARK 465 ALA T 2 |
| REMARK 465 VAL L 2 | REMARK 465 GLN T 3 |
| REMARK 465 ALA L 3 | REMARK 465 LYS T 4 |
| REMARK 465 LEU L 4 | REMARK 465 LYS T 5 |
| REMARK 465 ALA L 129 | REMARK 465 PRO T 6 |
| REMARK 465 LYS L 130 | REMARK 465 LYS T 7 |
| REMARK 465 THR L 131 | REMARK 465 LYS V 26 |
| REMARK 465 ALA L 132 | REMARK 465 LYS V 27 |
| REMARK 465 ALA L 133 | |
| REMARK 465 LYS L 134 | |
| REMARK 465 LYS L 135 | |
| REMARK 465 MET M 1 | |
| REMARK 465 MET N 1 | |
| REMARK 465 MET O 1 | |
| REMARK 465 ALA P 84 | |
| REMARK 465 ARG P 85 | |
| REMARK 465 GLU P 86 | |
| REMARK 465 GLY P 87 | |
| REMARK 465 ALA P 88 | |
| REMARK 465 MET Q 1 | |
| REMARK 465 MET R 1 | |
| REMARK 465 SER R 2 | |
| REMARK 465 THR R 3 | |
| REMARK 465 LYS R 4 | |
| REMARK 465 ASN R 5 | |
| REMARK 465 ALA R 6 | |
| REMARK 465 LYS R 7 | |
| REMARK 465 PRO R 8 | |
| REMARK 465 LYS R 9 | |
| REMARK 465 LYS R 10 | |
| REMARK 465 GLU R 11 | |

We claim:

1. A crystal of a 30S ribosomal subunit consisting of a tetragonal space group P4$_1$2$_1$2 with unit cell dimensions of a=401.375 Å, b=401.375 Å, c=175.887 Å.

2. A crystal of a 30S ribosomal subunit consisting of a tetragonal space group P4$_1$2$_1$2 with unit cell dimensions of a=401.4 Å, b=401.4 Å, c=175.9 Å.

3. A crystal of a 30S ribosomal subunit consisting of the structure defined by the co-ordinates of Table 1.

* * * * *

SEQUENCE LISTING

<160> NUMBER OF SEQ ID NOS: 1

<210> SEQ ID NO 1
<211> LENGTH: 20
<212> TYPE: PRT
<213> ORGANISM: artificial
<220> FEATURE:
<223> OTHER INFORMATION: zinc finger motif
<220> FEATURE:
<221> NAME/KEY: misc_feature
<222> LOCATION: (2)..(3)
<223> OTHER INFORMATION: X can be any amino acid
<220> FEATURE:
<221> NAME/KEY: misc_feature
<222> LOCATION: (5)..(16)
<223> OTHER INFORMATION: X can be any amino acid -continued

```
<220> FEATURE:
<221> NAME/KEY: misc_feature
<222> LOCATION: (18)..(19)
<223> OTHER INFORMATION: X can be any amino acid

<400> SEQUENCE: 1

Cys Xaa Xaa Cys Xaa Xaa Xaa Xaa Xaa Xaa Xaa Xaa Xaa Xaa Xaa Xaa
1               5                   10                  15

Cys Xaa Xaa Cys
            20
```